US010093702B2

(12) United States Patent
Li et al.

(10) Patent No.: US 10,093,702 B2
(45) Date of Patent: Oct. 9, 2018

(54) *METAPNEUMOVIRUS* IMMUNOGENS AND RELATED MATERIALS AND METHODS

(71) Applicants:Research Institute at Nationwide Children's Hospital, Columbus, OH (US); Ohio State Innovation Foundation, Columbus, OH (US)

(72) Inventors: Jianrong Li, Dublin, OH (US); Yongwei Wei, Ningbo (CN); Yu Zhang, Columbus, OH (US); Mark E. Peeples, Bexley, OH (US)

(73) Assignees: Research Institute at Nationwide Children's Hospital, Columbus, OH (US); Ohio State Innovation Foundation, Columbus, OH (US)

( * ) Notice: Subject to any disclaimer, the term of this patent is extended or adjusted under 35 U.S.C. 154(b) by 123 days.

(21) Appl. No.: 14/777,095

(22) PCT Filed: Mar. 14, 2014

(86) PCT No.: PCT/US2014/028443
§ 371 (c)(1),
(2) Date: Sep. 15, 2015

(87) PCT Pub. No.: WO2014/144153
PCT Pub. Date: Sep. 18, 2014

(65) Prior Publication Data
US 2016/0039884 A1     Feb. 11, 2016

Related U.S. Application Data

(60) Provisional application No. 61/790,707, filed on Mar. 15, 2013.

(51) Int. Cl.
*C07K 14/005*   (2006.01)
*A61K 39/155*   (2006.01)
*C07K 16/28*    (2006.01)
*A61K 39/12*    (2006.01)
*C12N 7/00*     (2006.01)
*A61K 39/00*    (2006.01)

(52) U.S. Cl.
CPC ............ *C07K 14/005* (2013.01); *A61K 39/12* (2013.01); *A61K 39/155* (2013.01); *C07K 16/2842* (2013.01); *C12N 7/00* (2013.01); *A61K 39/00* (2013.01); *A61K 2039/5254* (2013.01); *A61K 2039/543* (2013.01); *C07K 2317/76* (2013.01); *C12N 2760/18321* (2013.01); *C12N 2760/18333* (2013.01); *C12N 2760/18334* (2013.01)

(58) Field of Classification Search
None
See application file for complete search history.

(56) References Cited

U.S. PATENT DOCUMENTS

| 2004/0241188 A1 | 12/2004 | Collins et al. |
| 2005/0019891 A1 | 1/2005 | Fouchier et al. |
| 2009/0123529 A1 | 5/2009 | Li |

OTHER PUBLICATIONS

Cox et al., J. Virol. 2012 vol. 86: No. 22, pp. 12148-12160.*
Wei et al. J Virology, vol. 88, p. 4338-4352, 2014.*
Chang, Andres et al. "Human Metapneumovirus (HMPV) Binding and Infection Are Mediated by Interactions between the HMPV Fusion Protein and Heparan Sulfate." Journal of Virology, vol., No. 6, Mar. 2012, pp. 3230-3324, PMC. Web. Mar. 1, 2017.
International Preliminary Report on Patentability issued by the International Bureau of WIPO, dated Sep. 15, 2015 for International Application No. PCT/US2014/028443; 13 pages.
International Search Report and Written Opinion issued by the ISA/US, Commissioner for Patents, dated Nov. 5, 2014, for related Application No. PCT/US2014/028443; 19 pages.
Wei, Yongwei et al. "Roles of the Putative Integrin-Binding Motif of the Human Metapneumovirus Fusion (F) Protein in Cell-Cell Fusion, Viral Infectivity, and Pathogenesis." Ed. A. Garcia-Sastre. Journal of Virology, vol. 88, No. 8, Apr. 2014, pp. 4338-4352, PMC. Web. Mar. 1, 2017.

* cited by examiner

*Primary Examiner* — Shanon A. Foley
*Assistant Examiner* — Myron G Hill
(74) *Attorney, Agent, or Firm* — Faegre Baker Daniels LLP

(57) ABSTRACT

The present invention provides compositions useful to induce immune response to human *metapneumovirus*. Also provided are related materials and methods, including methods to induce an immune response in a mammal, comprising administering the compositions herein.

19 Claims, 20 Drawing Sheets
(12 of 20 Drawing Sheet(s) Filed in Color)
Specification includes a Sequence Listing.

FIG. 8

|  | Day 4 | Day 6 | Day 8 | Day 10 |
|---|---|---|---|---|
| Control No virus | | | | |
| rhMPV-R329K | | | | |
| rhMPV-G330A | | | | |
| rhMPV-D331A | | | | |
| rhMPV-D331E | | | | |
| rrhMPV-D331R | | | | |
| hMPV | | | | |

METAPNEUMOVIRUS IMMUNOGENS AND RELATED MATERIALS AND METHODS

CROSS REFERENCE TO RELATED APPLICATIONS

This application claims the benefit of International Application No. PCT/US2014/028443, filed Mar. 14, 2014, which claims priority from U.S. Provisional Application No. 61/790,707 filed Mar. 15, 2013, the disclosures of which are incorporated herein by reference in their entirety.

REFERENCE TO SEQUENCE LISTING SUBMITTED VIA EFS-WEB

This application is being filed electronically via the USPTO EFS-WEB server, as authorized and set forth in MPEP§ 1730 II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows: 53-54826-OSIF-2013-030_SL.txt, created on Mar. 14, 2014 and is 16,350 bytes in size.

BACKGROUND OF THE INVENTION

Human *metapneumovirus* (hMPV) is a member of the genus *Metapneumovirus* in the subfamily Pneumovirinae of the family Paramyxoviridae. HMPV was first identified in infants and children with acute respiratory tract infections in 2001 in The Netherlands. Soon after its discovery, hMPV was recognized as a globally prevalent pathogen. It is a major causative agent of acute respiratory tract disease in individuals of all ages, especially in infants, children, the elderly, and immunocompromised individuals. Epidemiological studies indicate that 5 to15% of all respiratory tract infections in infants and young children are caused by hMPV, a proportion second only to that of human respiratory syncytial virus (RSV). The clinical signs and symptoms associated with hMPV are similar to those of RSV, ranging from mild respiratory problems to severe coughs, bronchiolitis, and pneumonia. Currently, there are no therapeutics or vaccines available for hMPV. The only other member in the genus *metapneumovirus* is avian *metapneumovirus* (aMPV), which also is known as avian pneumovirus or Turkey Rhinotracheitis, is an economically important pathogen that causes acute respiratory disease in turkeys.

All viruses must cross the cell membrane to initiate infection. Paramyxoviruses enter host cells through the fusion of viral envelops with cellular membrane. Such fusion is mediated by viral glycoproteins that are located on the surface of virion envelope. For viruses in the Paramyxoviridae subfamily of the Paramyxoviridae family, membrane fusion requires both the attachment proteins (G, H, or HN) and the fusion (F) protein. Paramyxovirus F protein is a class I fusion protein, which is first synthesized as a precursor protein, F0, and subsequently cleaved into two disulfide-linked subunits, F1 and F2, by proteases in host cells. This cleavage generates a hydrophobic fusion peptide (FP), which is directly inserted into the membrane to initiate fusion. Paramyxovirus F proteins contain two conserved heptad repeat (HR) regions, the N-terminal heptad (HRA) and the C-terminal heptad (HRB), which are located downstream of the fusion peptide and upstream of the transmembrane (TM) domain, respectively. Upon triggering, the metastable pre-triggered F protein undergoes a series of dramatic and irreversible conformational changes. HRA and HRB are rearranged to form a highly stable six-helix bundle that brings two membranes together to initiate fusion.

Currently, the mechanism which triggers fusion so that it occurs at the right time and in the right place remain poorly understood. It is thought that binding of the attachment proteins to the cell surface receptor(s) induces conformational changes in F protein, which in turn triggers membrane fusion.

Membrane fusion of pneumoviruses is unique among the paramyxoviruses, in that fusion is accomplished by the F protein alone without help from the attachment glycoprotein. This attachment protein independent fusion activation has been well characterized in human respiratory syncytial virus (hRSV), bovine RSV (RSV), and ovine RSV. Recently, it was found that the F protein of hMPV, was able to induce fusion without the G protein. Recombinant hMPV lacking G protein was found to replicate efficiently in cell culture. Some hMPV strains require low pH, whereas fusion of all other paramyxoviruses occurs at neutral pH. In addition, fusion of hMPV requires trypsin.

F protein of hMPV alone is sufficient for induction of cell-cell fusion and viral entry indicating that hMPV F protein must possess dual functions, receptor binding and fusion promotion. It was found that integrin $\alpha v\beta 1$ is a functional receptor for hMPV. This is based on the observations that (i) $\alpha v\beta 1$ antibody inhibited hMPV infectivity; (ii) siRNA targeting $\alpha v\beta 1$ integrin blocked hMPV infectivity; (iii) F proteins of all known hMPV strains contain a putative integrin-binding motif ($^{329}$RGD$^{331}$); and (iv) a point mutation (D331E) in RGD motif inhibited binding of F protein to $\alpha v\beta 1$ integrin in host cells. In contrast, RGD is not essential for cell-cell fusion triggered by hMPV F protein. However, this conclusion is based on the observation that a single point mutation (D331E) in RGD motif in F protein did not significantly affect fusion activity and viral infectivity. Rather, heparin sulfate proteoglycans function as primary receptors for hMPV which is mediated by F, but not G protein. It was hypothesized that the interaction between integrins and hMPV occurs after the initial binding of hMPV F to heparan sulfate proteoglycans. This is consistent with the hypothesis that heparan sulfate serves as an adhesion factor for hMPV with subsequent integrin engagement being critical for entry. Nonetheless, molecular mechanisms underlying the interaction between hMPV F and integrin, and their roles in cell-cell fusion, viral binding, and hMPV life cycle have not been elucidated.

It would be beneficial to further elucidate the underlying mechanisms o hMPV and integrin interaction, and their roles in cell-cell fusion, viral binding, and hMPV life cycle. Also beneficial would be the development of hMPV vaccines

SUMMARY OF THE INVENTION

Described herein are compositions useful to induce immune response to human *metapneumovirus*. Also provided are related materials and methods, including methods to induce an immune response in a mammal, comprising administering the compositions and related materials described herein.

In a particular embodiment described herein is a composition comprising a nucleic acid molecule encoding a human *metapneumovirus* (hMPV) having a mutated integrin-binding motif (RGD motif) in a fusion (F) protein of hMPV, wherein the RGD motif is mutated as compared to wildtype hMPV.

In another embodiment described herein, the composition comprises a mutant nucleic acid molecule encoding an amino acid alteration in the hMPV F protein RGD motif as compared to wildtype hMPV and the amino acid mutation is selected from the group consisting of: nucleic acid mutation resulting in an amino acid sequence having an alanine substitution compared to wildtype; nucleic acid sense mutation resulting in a different amino acid having the same charge compared to wildtype; nucleic acid mutation resulting in a different amino acid having the opposite charge compared to wildtype; and nucleic acid mutations resulting in an aMPV fusion protein mimic.

In another embodiment described herein, the amino acid alteration is a nucleic acid mutation resulting in an amino acid sequence having an alanine substitution and/or a nucleic acid sense mutation resulting in a different amino acid having the same charge.

In another embodiment described herein, the mutated RGD motif comprises at least one nucleic acid mutation encoding an amino acid mutation selected from the group consisting of: R329K; G330A; D331A; D331E; and D331R.

In another embodiment described herein, the mutated RGD motif comprises a nucleic acid mutation encoding the amino acid mutation R329K and/or the mutation D331A.

In another embodiment described herein, the mutated RGD motif comprises a nucleic acid mutation encoding the amino acid mutation R329K.

In another embodiment described herein, the mutated RGD motif comprises a nucleic acid mutation encoding the amino acid mutation D331A.

In yet another embodiment described herein, the composition is a pharmaceutical composition.

In another embodiment described herein, the composition is a vaccine.

In a particular embodiment described herein is a method for inducing a protective immune response again human *metapneumovirus* (hMPV) in a mammal comprising administering to the mammal a pharmaceutically effective dose of the composition of claim 1.

In another embodiment described herein, the composition is administered orally, subcutaneously, or intranasally.

In another embodiment described herein, the mammal is selected from the group consisting of: cotton rat; and primate.

In another embodiment described herein, the mammal is a human.

In another embodiment described herein, the method for inducing a protective immune response again human *metapneumovirus* (hMPV) in a mammal further comprises administering at least one subsequent pharmaceutically effective dose of the composition to the mammal.

In another embodiment described herein, the at least one subsequent pharmaceutically effective dose is administered at a time interval selected from the group consisting of: approximately one week after the first dose; approximately two weeks after the first dose; approximately three weeks after the first dose; approximately four weeks after the first dose; approximately five weeks after the first dose; approximately six weeks after the first dose; approximately seven weeks after the first dose; and approximately eight weeks after the first dose.

In a particular embodiment described herein is a recombinant human *metapneumovirus* (hMPV) comprising a mutated integrin-binding motif (RGD motif) in a fusion (F) protein of hMPV capable of inducing neutralizing antibody and a T cell immune response in a mammal without inducing clinical symptoms of hMPV infection, wherein the RGD motif is mutated as compared to wild-type hMPV.

In another embodiment described herein, the RGD motif comprises at least one amino acid mutation selected from the group consisting of: alanine substitution compared to wildtype; substitution of at least one amino acid having the same charge compared to wildtype; substitution of at least one amino acid having the opposite charge as wildtype; and mutation resulting in an avian *metapneumovirus* (aMPV) F protein mimic.

In another embodiment described herein, the recombinant hMPV is selected from the group consisting of: rhMPV-R329K; rhMPV-G330A; rhMPV-D331A; rhMPV-D331E; and rhMPV-D331R.

In another embodiment described herein, the recombinant hMPV is rhMPV-R329K (SEQ ID NOS: 1-2).

In another embodiment described herein, the recombinant hMPV is rhMPV-D331A (SEQ ID NOS: 3-4).

In a particular embodiment described herein is a vaccine against human *metapneumovirus* (hMPV) infection comprising a recombinant hMPV, wherein the recombinant hMPV comprises a mutated integrin-binding motif (RGD motif) in a fusion (F) protein of hMPV.

In another embodiment described herein, the vaccine further comprises a pharmaceutically acceptable carrier, vehicle, and/or excipient.

In another embodiment described herein, the vaccine further comprises an adjuvant.

In a particular embodiment described herein is a method for inducing a protective immune response again human *metapneumovirus* (hMPV) in a mammal comprising administering to the mammal a pharmaceutically effective dose of the vaccine described herein.

In another embodiment described herein, the vaccine is administered orally, subcutaneously, or intranasally.

In another embodiment described herein, the method for inducing a protective immune response again human *metapneumovirus* (hMPV) in a mammal further comprises administering at least one subsequent pharmaceutically effective dose of the vaccine to the mammal.

In a particular embodiment described herein is a method to induce human *metapneumovirus* (hMPV)-neutralizing antibody in a mammal in need of such induction, comprising administering the composition of claim 1 to a mammal, thereby inducing hMPV-neutralizing antibody.

In another embodiment described herein, the induction of human *metapneumovirus* (hMPV)-neutralizing antibody attenuates or eliminates hMPV virulence upon challenge by virulent wildtype hMPV.

In another embodiment described herein, the induction of human *metapneumovirus* (hMPV)-neutralizing antibody results in a T cell immune response upon challenge by virulent wildtype hMPV.

In a particular embodiment described herein is a method to induce a T cell immune response in a mammal in need of such induction, comprising administering a composition described herein to a mammal, thereby inducing a T cell immune response.

In another embodiment described herein, the induction of the T cell response attenuates or eliminates hMPV virulence upon challenge by virulent wildtype hMPV.

In another embodiment described herein, the induction of the T cell response results in immunogenic protection upon challenge by virulent wildtype hMPV.

In a particular embodiment described herein is a method to inhibit wildtype human *metapneumovirus* (hMPV) replication in a mammal in need of such inhibition, comprising administering a composition described herein to a mammal, thereby inhibiting hMPV replication.

In another particular embodiment described herein is a method of preparing a pharmaceutical composition for inducing a protective immune response against human *metapneumovirus* (hMPV) in an individual in need thereof comprising mixing a composition of claim 1 with a suitable carrier, vehicle, and/or excipient, thereby forming a pharmaceutical composition.

In another embodiment described herein, the pharmaceutical composition is formulated for oral, subcutaneous, or intranasal administration.

In a particular embodiment described herein is an immunogenic composition comprising an attenuated, avirulent human *metapneumovirus* (hMPV) strain, wherein the attenuated, avirulent hMPV strain is selected from the group consisting of: the attenuated hMPV rhMPV-R329K deposited with the American Type Culture Collection (ATCC); and the attenuated hMPV rhMPV-D331A deposited with the ATCC.

In another embodiment described herein, the immunogenic composition further comprises a pharmaceutically acceptable carrier, vehicle, and/or excipient.

In another embodiment described herein, the immunogenic composition further comprises an adjuvant.

In another embodiment described herein, the immunogenic composition elicits or provokes an immune response when administered to a mammal.

In a particular embodiment described herein is a method for inducing a protective immune response again human *metapneumovirus* (hMPV) in a mammal comprising administering to the mammal a pharmaceutically effective amount of attenuated, avirulent human *metapneumovirus* (hMPV) strain, wherein the attenuated, avirulent hMPV strain is selected from the group consisting of: the attenuated hMPV rhMPV-R329K deposited with the American Type Culture Collection (ATCC); and the attenuated hMPV rhMPV-D331A deposited with the ATCC.

In another embodiment described herein, the attenuated, avirulent hMPV strain is administered orally, subcutaneously, or intranasally.

In a particular embodiment described herein is a method of producing an immunogenic composition, comprising admixing attenuated, avirulent human *metapneumovirus* (hMPV) strain, wherein the attenuated hMPV strain is selected from the group consisting of: the attenuated hMPV rhMPV-R329K deposited with the American Type Culture Collection (ATCC); and the attenuated hMPV rhMPV-D331A deposited with the ATCC, with a pharmaceutically acceptable carrier, vehicle, and/or excipient.

In another particular embodiment described herein is a method of attenuating a human *metapneumovirus* (hMPV) comprising mutating an integrin-binding motif (RGD motif) in a fusion (F) protein of the hMPV, wherein the RGD motif comprises at least one amino acid mutation selected from the group consisting of: alanine substitution compared to wild-type; substitution of at least one amino acid having the same charge compared to wildtype; substitution of at least one amino acid having the opposite charge as wildtype; and mutation resulting in an avian *metapneumovirus* (aMPV) F protein mimic, wherein the RGD motif is mutated as compared to wild-type hMPV, and wherein mutation of the RGD mutation results in attenuation of the hMPV.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 2A) Knockdown of integrins $\alpha 5$ and $\alpha V$ expression by siRNA. Twenty pmoles of synthetic siRNAs targeting human integrin subtypes $\alpha 5$ or $\alpha v$ as well as control siRNA were transfected into Vero E6 cells in 24-well plates using Oligofectamine reagents according to the manufacturer's instructions. After 48 h post-transfection, the expression of $\alpha 5$ or $\alpha v$ was detected by Western blot. FIG. 2B) Syncytium formation induced by F protein of hMPV after knockdown integrins $\alpha 5$ and $\alpha V$. Vero E6 cells in 24-well plates were transfected with twenty pmoles of synthetic siRNAs targeting human integrin subtypes $\alpha 5$ or $\alpha v$ as well as control siRNA. After treatment with siRNAs for 24 h, Vero E6 cells were transfected with 0.8 μg of pCAGGS-F using Lipofectamine Plus reagents, and then subjected to pH pulses (pH 5.0). At 48 h, monolayers were fixed with methanol and stained with Giemsa. FIG. 2C) Quantitation of syncytium formation after knockdown integrins $\alpha 5$ and $\alpha V$. The number of syncytium ($\geq 4$ nuclei in each syncytium) was counted under microscope using six randomly selected fields in each siRNA treated or untreated well. The mean number of syncytium per field for each treatment was calculated. The percent of fusion for each siRNA treatment was normalized by the mean number of syncytium in cells transfected with pCAGGS-F without siRNA treatment. Data shown are averages for three independent experiments.

FIG. 4A) hMPV had defects in infectivity in integrin-deficient cell line. Confluent monolayers of GD1286 or GD25 cells in 24-well plates were incubated at 4° C. for 30 min. The cells were infected with 100 PFU of hMPV per well. After incubation on ice for 1 h (shake every 15 min), the inoculum was removed, and the cells were washed with cold DMEM for 3 times. The infected cells were then incubated with fresh medium at 37° C. and 5% CO2. After 24 h, the binding capacity was determined by counting immunostaining spots. Percent of infectivity in GD 25 cells was normalized by the infectivity of hMPV in GD1286 cells. Data shown are averages for three independent experiments. FIG. 4B) hMPV formed much smaller immunospots in integrin-deficient cell line. Confluent monolayers of GD1286 or GD25 cells were infected with hMPV. After 24 h, immunostaining assay was performed, and immunospots formed by hMPV were visualized.

FIG. 5A) Syncytium formation of hMPV F proteins carrying mutations at RGD motif. Confluent monolayers of Vero E6 cells were transfected with 2 μg plasmids of pCAGGS-F or F mutants. At 24 h posttransfection, the monolayers were fixed with methanol and stained with Giemsa stain. FIG. 5B) Content mixing fusion assay for hMPV F mutants. The extent of fusion for each F mutant was quantitated with the content-mixing fusion assay at pH 5.0 and normalized by the fusion of wild type hMPV F protein. Data shown are averages for three independent experiments. FIG. 5C) Cell surface expression of hMPV F mutants. Cell surface expression was determined by FACS using monoclonal antibody against hMPV F protein and normalized by the expression level of wild type F protein at cell surface.

FIG. 8: Single step growth curve of recombinant hMPVs carrying mutations in RGD motif. Vero E6 cells in 35-mm dishes were infected with each recombinant hMPV at MOI=0.01. After adsorption for 1 h, the inoculums were removed and the infected cells were washed 3 times with OPTI-MEM. Then, fresh OPTI-MEM containing 2% FBS was added and cells were incubated at 37° C. for various time periods. Aliquots of the cell culture fluid were removed at the indicated intervals. Viral titer was determined by an immunostaining assay in Vero-E6 cells.

FIG. 9: Cytopathic effects (CPE) caused hMPVs carrying mutations in RGD motif. Vero E6 cells were infected with each recombinant hMPV at MOI=0.01. CPE was monitored on daily basis. Pictures were taken at days 4, 6, 8, and 10 post-infection.

Figure 10:
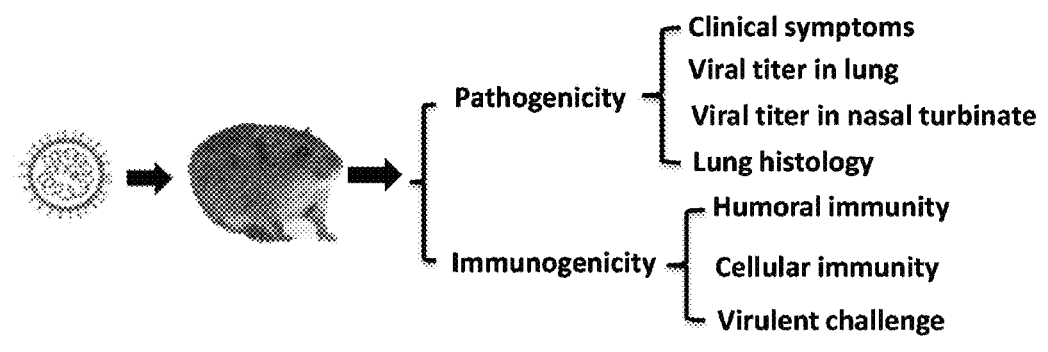

FIG. 10: Evaluation of pathogenicity and immunogenicity of hMPV mutants in cotton rats. All recombinant viruses were inoculated into four-week-old specific-pathogen-free cotton rats. After inoculation, the animals were evaluated on a daily basis for mortality, weight loss, and the presence of any respiratory symptoms of hMPV. At day 4 post-infection, five cotton rats from each group were sacrificed, and their lungs were removed for pathogenicity studies as follows. (i) Lung virus titer. Nasal turbinate and one lung from each animal were weighed and homogenized in 1 ml of phosphate-buffered saline (PBS). Viral titer was determined by plaque assay. (ii) Pulmonary histopathology. One lung from each mouse was inflated with 10% buffered formalin, embedded in paraffin, sectioned, and stained with hematoxylin-eosin. Histopathological changes were scored, and include the extent of inflammation (focal or diffuse), the pattern of inflammation (peribronchilolar, perivascular, interstitial, alveolar), and the nature of the cells making up the infiltrate (neutrophils, eosinophils, lymphocytes, macrophages). Deparaffinized sections were also stained with polyclonal antiserum to determine the distribution of viral antigen. Five animals per cohort were used in these experiments.

FIG. 11: Recombinant hMPVs triggered a high level of neutralizing antibody titer in cotton rats. Cotton rats were immunized each recombinant hMPV intranasally at a dose of $2.0 \times 10^5$ PFU per rat. Blood samples were collected from each rat weekly by retro-orbital bleeding. The hMPV neutralizing antibody was determined using a plaque reduction neutralization assay as described in Materials and Methods.

FIG. 12: Lung histology of recombinant hMPVs. Right lung from each cotton rat was preserved in 4% (v/v) phosphate-buffered paraformaldehyde. Fixed tissues were embedded in paraffin, sectioned at 5 microns, and stained with hematoxylin-eosin (HE) for the examination of histological changes by light microscopy.

FIG. 14A) The predicted hMPV F protein monomer. Structure was predicted using Modeller 9.0 based on the prefusion crystal structure of RSV F protein (PDB ID: 4JHW) as template. The putative integrin binding site (R329 and D331) are highlighted. FIG. 14B) The predicted hMPV F protein trimer. The F trimer with the surface of each monomer was highlighted in a different color. The RGD motif is located on the contact region of each subunit of the F trimer. FIG. 14C) The location of RGD motif in hMPV F protein monomer. Partial structure of hMPV F containing DI, DII and DIII was solved (PDB ID: 4DAG). The location of RGD motif was highlighted. FIG. 14D) The location of RGD motif in hMPV F protein trimer. The F trimer with the surface of each monomer was highlighted in a different color.

DETAILED DESCRIPTION OF THE INVENTION

Figure 1A:
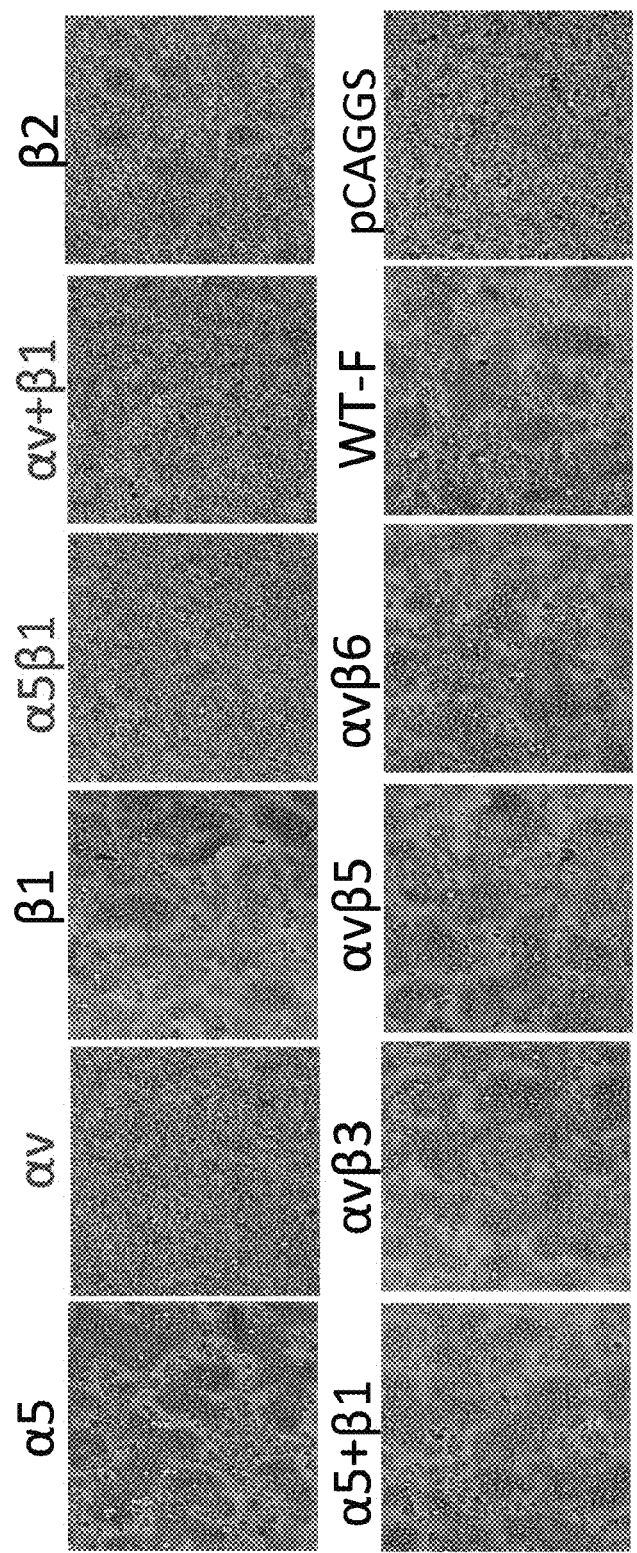
FIG. 1A: $\alpha 5\beta 1$ and $\alpha v$ integrin-specific antibodies block cell-cell fusion triggered by hMPV F protein. Syncytia formation induced by hMPV F protein expression in the presence of integrin antibodies. Vero E6 cells in 48-well plates were transfected with 0.8 μg of pCAGGS-F or pCAGGS. After incubation with a plasmid-Lipofectamine mixture for 8 h, cells continued to grow in OPTI-MEM containing 10 μg/ml of integrin antibody and 0.2 μg/ml of TPCK-trypsin. At 48 h, monolayers were fixed with methanol and stained with Giemsa. Syncytia are indicated by arrows.

The inventors demonstrate herein that α5β1 and αv integrins are important for cell-cell fusion triggered by hMPV F protein. Moreover, amino acid residues R329 and G330 within the putative integrin-binding motif ($^{329}$RGD$^{331}$) in hMPV F protein play crucial roles in cell-cell fusion and receptor binding. This conclusion is supported by multiple lines of evidence. First, cell-cell fusion was inhibited by incubation with integrin α5β1 or αv-specific antibodies as well as siRNA-mediated knockdown of α5 or αv expression. Second, integrin α5β1 or αv-specific antibodies reduced hMPV infection, and expression of integrin α5β1 on the cell surface enhanced the binding of hMPV to host cells and viral infectivity. Third, amino acid substitutions in R329 and G330 within RGD motif in F protein significantly impaired fusion activity. Finally, soluble hMPV F proteins carrying mutations in the RGD motif were defective in host cell binding.

The inventors have generated a panel of recombinant hMPVs carrying mutations in the integrin binding motif (RGD). These viral mutants include rhMPV-R329K, G330A, G330S, D331A, D331R, and D331E. These recombinant hMPVs are attenuated in cell culture based on plaque morphology, immunostaining assay, cytopathic effect (CPE), and viral growth curve. Recombinants rhMPV-R329K and D331A are highly attenuated in cotton rats. These recombinant hMPVs did not cause any clinical symptoms or lung histological damages, and had low to no viral titer in nasal turbinate or lungs in cotton rats. Furthermore, these recombinant hMPVs triggered high titer of neutralizing antibody and T cell immune response, and protected cotton rats from virulent challenges.

Definitions

As used herein, the following terms shall have the meanings set forth:

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. "Antibody" may to refer to any antibody-like molecule that has an antigen binding region, and includes antibody fragments such as Fab', Fab, F(ab')2, single domain antibodies (DABs), Fv, scFv (single chain Fv), and the like.

As used herein, "immunogen" refers to any substance that is capable of being the target of an immune response, for example, an antigen. An immunogen may be the target of, for example, a cell-mediated and/or humoral immune response raised by a subject organism. Alternatively, an immunogen may be the target of a cellular immune response (e.g., immune cell maturation, production of cytokines, production of antibodies, etc.).

As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another.

"Immunostimulatory combination" refers to any combination of components that can be co-administered to provide a therapeutic and/or prophylactic immunostimulatory effect. The components of an immunostimulatory combination can include, but are not limited to, cells, antigens, adjuvants, and the like.

"Composition" refers to any mixture, aqueous or non-aqueous solution, suspension, emulsion, gel, cream, food, or the like, that contains two or more components. The components may be, for example, two immunostimulatory components that, together, provide an immunostimulatory combination. The immunostimulatory components may be any combination of one or more antigens, one or more adjuvants, or both. For example, a composition may include two adjuvants so that the composition forms an adjuvant combination. Alternatively, a composition may include an adjuvant combination and an antigen so that the mixture forms, e.g. a vaccine.

As used herein, the term "pharmaceutical composition" encompasses a product comprising one or more active ingredients, and an optional carrier, vehicle, or excipient comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. Generally, pharmaceutical compositions are prepared by uniformly and intimately bringing the active ingredient into association with a liquid carrier, vehicle, or excipient, or a finely divided solid carrier, vehicle, or excipient, or both, and then, if necessary, shaping the product into the desired formulation. The pharmaceutical composition includes enough of the active ingredient to produce the desired effect. Accordingly, the pharmaceutical compositions described herein encompass any composition made by admixing a compound or recombinant human *metapneumovirus* of the present invention and a pharmaceutically acceptable carrier, vehicle, or excipient. By "pharmaceutically acceptable" it is meant the carrier, vehicle, or excipient must be compatible with the other ingredients of the formulation and not deleterious to the recipient thereof.

In certain embodiments, the one or more active ingredients may be an antigen.

"Synergistic" and variations thereof refer to activity (e.g., immunostimulatory activity) of administering a combination of compounds that is greater than the additive activity of the compounds if administered individually.

"Vaccine" refers to a pharmaceutical composition that includes an antigen. A vaccine may include components in addition to the antigen such as, for example, one or more adjuvants, a carrier, etc.

In some embodiments, an immunostimulatory combination may further include an antigen. When present in the immunostimulatory combination, the antigen may be administered in an amount that, in combination with the other components of the combination, is effective to generate an immune response against the antigen. For example, the antigen can be administered in an amount from about 100 ng/kg to about 100 mg/kg. In many embodiments, the antigen may be administered in an amount from about 10 μg/kg to about 10 mg/kg. In some embodiments, the antigen may be administered in an amount from about 1 mg/kg to about 5 mg/kg. The particular amount of antigen that constitutes an amount effective to generate an immune response, however, depends to some extent upon certain factors such as, for example, the particular antigen being administered; the state of the immune system; the method and order of administration, and the antigen; the species to which the formulation is being administered; and the desired therapeutic result. Accordingly, it is not practical to set forth generally the amount that constitutes an effective amount of the antigen. Those of ordinary skill in the art, however, can readily determine the appropriate amount with due consideration of such factors.

When present, the antigen may be administered simultaneously or sequentially with any component of the immunostimulatory combination. Thus, the antigen may be administered alone or in a mixture with one or more adjuvants. In some embodiments, an antigen may be administered simultaneously (e.g., in a mixture) with respect to one adjuvant, but sequentially with respect to one or more additional adjuvants.

Sequential co-administration of an antigen and other components of an immunostimulatory combination can include cases in which the antigen and at least one other component of the immunostimulatory combination are administered so that each is present at the treatment site at the same time, even though the antigen and the other component are not administered simultaneously. Sequential co-administration of the antigen and the other components of the immunostimulatory combination also can include cases in which the antigen or at least one of the other components of the immunostimulatory combination is cleared from a treatment site, but at least one cellular effect of the cleared antigen or other component (e.g., cytokine production, activation of a certain cell population, etc.) persists at the treatment site at least until one or more additional components of the combination are administered to the treatment site. Thus, it may be possible that an immunostimulatory combination of the invention can, in certain circumstances, include one or more components that never exist in a mixture with another component of the combination.

Numbering of amino acids, unless otherwise specified, is of amino acids comprising the human *metapneumovirus* fusion protein (hMPV F protein). The first amino acid (from the N-terminus) of hMPV F protein is designated amino acid 1. For example, R329 indicates the presence of arginine at amino acid position 329 of the hMPV F protein, and the notation R329K indicates the substitution of arginine at position 329 by lysine.

The invention also provides a method of treating a viral infection in an animal comprising administering a therapeutically effective amount of an immunostimulatory composition of the invention to the animal. A therapeutically effective amount to treat or inhibit a viral infection is an amount that will cause a reduction in one or more of the manifestations of viral infection, such as viral lesions, viral load, rate of virus production, and mortality as compared to untreated control animals.

EXAMPLES

The methods and embodiments described herein are further defined in the following Examples. Certain embodiments of the present invention are defined in the Examples herein. It should be understood that these Examples, while indicating preferred embodiments of the invention, are given by way of illustration only. From the discussion herein and these Examples, one skilled in the art can ascertain the essential characteristics of this invention and without departing from the spirit and scope thereof, can make various changes and modifications of the invention to adapt it to various usages and conditions.

Part I. Roles of the putative integrin-binding motif of the human *metapneumovirus* fusion (F) protein in cell-cell fusion, viral infectivity, and pathogenesis, and Recombinant human *metapneumovirus* carrying mutations in the integrin-binding motif as live attenuated vaccines Example 1

Materials and Methods

Cells. Vero E6 cells (ATCC no. CRL-1586), GD25 cells, GD1286 cells and BHK-SR19-T7 cells were grown in Dulbecco's modified Eagle's medium (DMEM: Invitrogen, Carlsbad, Calif.) supplemented with 10% (v/v) fetal bovine serum (FBS; Invitrogen). The medium of the BHK-SR19-T7 cells was supplemented with 10 μg/ml neomycin (Invitrogen) every other passage to select for T7 polymerase-expressing cells. LLC-MK2 cells were grown in OPTI-modified Eagle's medium (OPTI-MEM; Invitrogen) supplemented with 2% (v/v) FBS. Cells were grown at 37° C. in a 5% $CO_2$ humidified incubator.

Antibodies. Integrin-specific monoclonal antibodies MAB2021Z (αv, clone AV1), MAB1959 (β1, clone P5D2), MAB1389 (β2, clone WT.3), MAB1976Z ($α_vβ_3$, clone LM609), MAB1961 ($α_vβ_5$, clone P1F6), MAB2077Z ($α_vβ_6$, clone 10D5), MAB1956Z (α5, clone P1D6) and MAB1969 (α5β1, clone JBS5) were purchased from Millipore (Billerica, Mass.). Monoclonal antibody against hMPV F protein (M3884-4C, clone 9i11) was purchased from USBiological company. hMPV N protein-specific monoclonal antibody (MAB80138, clone 507) and goat anti-Mouse FITC-conjugated IgG (H+L) antibody (12-506) were purchased from Millipore (Billerica, Mass.). Goat Anti-Mouse IgG (H+L), Peroxidase Conjugated antibody was purchased from Thermo Scientific (Rockford, Ill.).

Plasmids and site-directed mutagenesis. A plasmid (phMPV) encoding the full-length genomic cDNA of hMPV lineage A strain NL/1/00 was kindly provided by Dr. Ron A. M. Fouchier at Erasmus Medical Center, Rotterdam, the Netherlands. The F gene was amplified from plasmid phMPV using Supermix polymerase (Qiagen, Valencia, Calif.), digested by EcoR I and Xho I and cloned into pCAGGS at the same sites, which resulted in the construction of pCAGGS-F. The F gene mutations were generated by site-directed mutagenesis using phMPV or pCAGGS-F as template by the QuikChange methodology (Stratagene, La Jolla, Calif.) (Table 1). The presence of the desired mutation was verified by sequencing.

Fusion staining assay. Monolayers of Vero E6 cells in 6-well plates were transfected with 2 μg of each plasmid using Lipofectamine (Invitrogen) according to the manufacturer's instructions. After transfection, the cells continued to grow in 2 ml of OPTI-MEM (Invitrogen) for 24 h, and then were washed and incubated at 37° C. in OPTI-MEM containing 0.2 µg/ml TPCK (L-1-tosylamide-2-phenylethyl chloromethyl ketone)-trypsin for another 2 h. Since fusion of hMPV lineage A strain NL/1/00 F protein is low pH dependent, all fusion assays were subjected to low pH pulses. The cells were washed four times with phosphate-buffered saline (PBS, pH 5.0) supplemented with 10 mM HEPES and 5 mM MES (morpholine ethanesulfonic acid). Each washing cycle lasted for 4 min followed by incubation in 2 ml of OPTI-MEM for 2 h. After pH pulses, the cells continued to grow in 2 ml of fresh OPTI-MEM till 48 h post-transfection. Finally, the cells were fixed with methanol and syncytia were visualized by Giemsa staining. Digital photographs of syncytia were taken under a Nikon TS100 inverted phase-contrast microscope mounted with a Nikon Coolpix995 camera.

Fusion inhibition assay. Confluent monolayers of Vero E6 cells in a 48-well plate were transfected with pCAGGS-F, pCAGGS-F mutants, or pCAGGS (as control). For cells in each well, the transfection mixture contained 0.8 µg of plasmids, 200 µl of OPTI-MEM, and 0.2 µl of Lipofectamine. After incubation with the transfection mixture for 6-8 h, cells continued to grow in OPTI-MEM (with 10 µg/ml of selected integrin antibodies) for 24 h. Subsequently, cells were subjected to four cycles of low pH pulses. The cells were washed four times with PBS (pH 5.0) supplemented with 10 mM HEPES and 5 mM MES. Each washing cycle lasted for 4 mM followed by incubation in 2 ml of OPTI-MEM containing 5 µg/ml of selected integrin antibodies and 0.2 µg/ml of TPCK-trypsin for 2 h. The cells continued to grow in OPTI-MEM (with 5 µg/ml of selected integrin antibodies and 0.2 µg/ml of TPCK-trypsin) for another 12 h followed by cell fixation and syncytia visualization.

Integrin-targeting siRNA transfection. Twenty pmoles of either synthetic siRNAs targeting human integrin subtypes α5 (sc-29372, Santa Cruz Biotechnology, CA), αv (sc-29373, Santa Cruz Biotechnology) or control siRNA (sc-37007, Santa Cruz Biotechnology) were transfected into Vero E6 cells (at the confluency of 75%) in 24-well plates using Oligofectamine reagents (Invitrogen) according to the manufacturer's instructions. After treatment with siRNAs for 24 h, Vero E6 cells were transfected with 0.8 µg of pCAGGS-F using Lipofectamine Plus reagents (Invitrogen) for 8 h as described above, and then subjected to pH pulses followed by visualization of syncytia.

Content mixing assay for fusion. Confluent Vero E6 cells in 6-well plates were co-transfected with 2 µg each of a plasmid containing the hMPV F gene (pCAGGS-F or F mutant) and a plasmid (pGINT7β-gal) encoding a β-galactosidase gene under the control of T7 promoter. At 24 h post-transfection, the cells were detached with trypsin, washed twice with DMEM, and resuspended in DMEM plus 10% FBS. The plasmid-transfected cells were mixed with equal numbers of BHKT7 cells which constitutively express T7 RNA polymerase. After incubation at 37° C. for another 24 h, the cells were washed 4 times with PBS (pH 5.0) containing 10 mM HEPES and 5 mM MES. Where indicated, the fusion assay was performed in the presence of 10 µg/ml of selected integrin antibodies. The cells were lysed by Nonidet P40 solution (0.5%). The extent of fusion was quantitated by measuring the β-galactosidase activity using a plate reader (Molecular Devices, Sunnyvale, Calif.). The fusion activity of the F mutants was determined as a percentage of the β-galactosidase production observed in cells expressing wild-type (wt) F protein.

Cell surface expression. Surface expression of the wt and mutant F proteins was assayed by fluorescence-activated cell sorting (FACS). Six-well plates were seeded with Vero E6 cells at a density of 1×10$^6$ cells/well. Transfection was performed using Lipofectamine Plus reagents (Invitrogen) according to the manufacturer's instructions. At 48 h post-transfection, the cells were washed twice with 3% FBS in PBS and incubated in primary monoclonal antibody against hMPV F protein (1:50 diluted in 3% BSA/PBS) for 1 h at 37° C. After being washed with FACS medium, cells were incubated with goat anti-mouse FITC-conjugated secondary antibody (1:100 in 3% BSA/PBS) for 1 h at 37° C. The cells were washed again, detached with EDTA, and washed two more times. Finally, the cells were resuspended in 500 µl of fix solution (2% paraformaldehyde, 1% FBS in PBS), and subjected to FACS analysis using Becton Dickinson FACSCalibur analyzer with CellQuest software. By comparison to a negative control, only positive cells were gated to estimate the geometric mean fluorescence intensity to evaluate the cell surface expression level. The results were normalized to percent of the wt control set at 100%.

Recovery of recombinant hMPV. Recovery of recombinant hMPV from the infectious clones was performed. rhMPV was recovered by co-transfection of a plasmid encoding the full-length genomic cDNA of hMPV NL/1/00 (phMPV) and support plasmids encoding viral N (pCITE-N), P (pCITE-P), L (pCITE-L), and M2-1 (pCITE-M2-1) proteins into BHK-SR19-T7 cells which express stably the T7 RNA polymerase. Six days post-transfection the cells were subjected to three freeze-thaw cycles followed by centrifugation at 3,000×g for 10 min. The supernatant was used subsequently to infect new LLC-MK2 cells. Since hMPV requires trypsin to grow, TPCK-trypsin was added to the media to the final concentration of 0.1 μg/ml at day 2 post-infection. Cytopathic effects (CPE) were observed 5 days post-infection and the recovered viruses were amplified further in LLC-MK2 cells. The recovery of recombinant virus was confirmed by immunostaining and direct agarose overlay plaque assays.

Immunostaining of recombinant hMPV. Immunostaining was used for virus titration. LLC-MK2 or Vero-E6 cells (at the confluency of 90%) in a 96-well plate were inoculated with 10-fold serial dilutions of recombinant hMPV mutants and incubated at 37° C. for 1 h. Infected cells were cultured in fresh OPTI-MEM media (0.2 ml per well) at 37° C. At day 4 post-infection, the supernatant was removed and cells were fixed in a pre-chilled acetone:methanol solution (at the ratio of 3:2) at room temperature (RT) for 15 min. Cells were permeablized in a phosphate saline buffer (PBS) containing 0.4% Triton X-100 at RT for 10 min, and blocked at 37° C. for 1 h using 1% bovine serum albumin (BSA) in PBS. The cells were then labeled with an anti-hMPV N protein primary monoclonal antibody (Millipore, Billerica, Mass.) at dilution of 1:1,000, followed by incubation with horseradish peroxidase (HRP)-labeled rabbit anti-mouse secondary antibody (Thermo Scientific, Waltham, Mass.) at dilution of 1:5,000. After incubation with AEC substrate chromogen (Sigma, St. Louis, Mo.), positive cells were then visualized under the microscope. Positive plaques were counted to determine viral titers.

Production and purification of soluble $His_6$-tagged (SEQ ID NO: 5) F ectodomain. Monolayers of Vero E6 cells were transfected with pCAGGS-sF or mutants using Lipofectamine (Invitrogen) according to the manufacturer's instructions. After 48 h post-transfection, the supernatant and cells were harvested separately. Supernatant was filtered through 0.2-μm-pore-size filters before purification. Cells were lysed in buffer consisting of 50 mM Tris-Cl, 140 mM NaCl, 1.5 mM $MgCl_2$, 0.5% NP-40, and phenylmethylsulfonyl fluoride protease inhibitor cocktail (Invitrogen) and were clarified by centrifugation (30,000×g, 10 min). The expression of sF protein in cell lysate and supernatant was confirmed Western blotting. Purification of the soluble His-tagged F ectodomain (SEQ ID NO: 5) was performed using a $Ni^{2+}$ column (Qiagen). The cell lysates or supernatant were incubated with Ni-nitrilotriacetic acid (NTA)-agarose beads (Qiagen) for 2 h. The resin was then washed with 20 bed volumes of wash buffer (50 mM $NaH_2PO_4$, 10% glycerol, 300 mM NaCl, 20 mM imidazole [pH 8.0]), and the His-tagged proteins were eluted in elution buffer (50 mM $NaH_2PO_4$, 10% glycerol, 300 mM NaCl, 250 mM imidazole [pH 7.0]). Where indicated, the His-tagged sF proteins were purified further by ion-exchange chromatography through a Mono S HR 5/5 column (GE Healthcare). The purified proteins were separated by 10% sodium dodecyl sulfate-polyacrylamide gel electrophoresis (SDS-PAGE) and visualized by Coomassie blue stain. Protein amounts were determined by Bradford assay.

Agarose overlay plaque assay for recombinant hMPV mutants. The agarose overlay plaque assay was used for determination of the plaque size of recombinant hMPV. Vero E6 cells were seeded into six-well plates (Corning Life Sciences, Wilkes-Barre, Pa.) at a density of $2\times10^6$ cells per well. After incubation for 18 h, the medium was removed and cell monolayers were infected with 400 µl of a 10-fold dilution series of each virus. After incubation at 37° C. for 1 h with agitation every 10 min, the cells in each well were overlaid with 2.5 ml of Eagle minimum essential medium (MEM) containing 1% agarose, 1% FBS, 0.075% sodium-bicarbonate ($NaHCO_3$), 20 mM HEPES (pH 7.7), 2 mM L-Glutamine, 12.5 mg/mL of penicillin, 4 mg/mL of streptomycin, and 4 mg/mL of kanamycin. The plates were incubated at 4° C. for 30 min to solidify the overlay media. After incubation at 37° C. and 5% $CO_2$ for 6 days, the cells were fixed in 10% (v/v) formaldehyde for 2 h, and the plaques were visualized by staining with 0.05% (wt/vol) crystal violet.

Virus-cell infectivity (blocking) assays. Confluent monolayers of LLC-MK2 cells in 48-well plates were infected with each virus at an MOI of 100 per well. After incubation on ice for 1 h (with gentle shaking every 15 min), the inoculum was removed and the unbound viruses were removed by washing with OPTI-MEM three times. The infected cells were then incubated with fresh OPTI-MEM at 37° C. and 5% $CO_2$. Twenty-four hours after infection, immunostaining was performed and the positive spots were counted under the microscope. For virus-cell infectivity blocking assays, the cells were pretreated with integrin antibody (20 µg/ml) at 37° C. for 1 h. The cells were then infected and analyzed by immunostaining.

Single step virus growth of recombinant hMPV. Viral growth was determined using an immunostaining assay on Vero-E6 cells. Confluent Vero-E6 cells in 35-mm dishes were infected with each recombinant hMPV at an MOI of 0.01. After adsorption for 1 h, the inoculum was removed and the cells were washed with 2 ml of OPTI-MEM. Subsequently, fresh OPTI-MEM (supplemented with 2% FBS) was added and infected cells were incubated at 37° C. for various time periods. Aliquots of the cell culture fluid were removed at the indicated intervals and the viral titer was determined by immunostaining assay on Vero-E6 cells.

Virus-cell binding assays. Confluent monolayers of LLC-MK2 cells in 48-well plates were infected with each virus at an MOI of 100 per well. After incubation on ice for 1 h (with gentle shaking every 15 min), the inoculum was removed, and the unbound viruses were removed by washing the cells with OPTI-MEM three times. The infected cells were then incubated with fresh OPTI-MEM at 37° C. and 5% $CO_2$. Twenty-four hours after infection, immunostaining was undertaken as described above. The positive cell spots were counted under the microscope.

Infectivity of recombinant hMPV in a cotton rat model. Thirty four-week-old female specific-pathogen-free cotton rats (Harlan Laboratories, Indianapolis, Ind.) were randomly divided into six groups (5 rats per group). These cotton rats were housed within ULAR facilities of The Ohio State University and used under an animal use protocol approved by the Institutional Animal Care and Use Committee (IACUC). Each group was separately housed under BSL-2 conditions. Rats in group 1 were inoculated with $2.0\times10^5$ PFU of the wild type hMPV and served as a positive control. Rats in groups 2-5 were inoculated with $2.0\times10^5$ PFU of four hMPV mutants (rhMPV-R329K, D331A, D331E, and D331R). Rats in group 6 were inoculated with cell culture medium (DMEM) and served as uninfected controls (the normal control). Each rat was inoculated intranasally at a dose of $2.0\times10^5$ PFU in isoflurane narcosis with a volume of 100 µl. After inoculation, the animals were evaluated on a daily basis for mortality, weight loss, and the presence of any respiratory symptoms of hMPV. At day 4 post-infection, cotton rats were sacrificed, and their lungs and nasal turbinate were collected for both virus isolation and histological analysis as described below.

Immunogenicity of recombinant hMPV in cotton rats. Thirty four-week-old female specific-pathogen-free cotton rats (Harlan Laboratories, Indianapolis, Ind.) were randomly divided into five groups (5 rats per group). Rats in groups 1-3 were immunized with wildtype rhMPV, rhMPV-R329K, and D331A, respectively. Rats in group 4 were inoculated with DMEM and served as the unimmunized but challenged control. Rats in group 5 were inoculated with DMEM and served as the uninfected control (normal control). All rats were immunized intranasally at a dose of $2.0\times10^5$ PFU per rat. After immunization, the animals were evaluated daily for body weight, mortality and the presence of any symptoms of hMPV infection. Blood samples were collected from each rat weekly by retro-orbital bleeding under isofluorane narcosis, and serum was separated for antibody detection. At week 4 post-immunization, rats in groups 1-5 were challenged intranasally with wild type hMPV at a dose of $1.0\times10^6$ PFU per rat. After challenge, the animals were evaluated twice every day for mortality and the presence of any symptoms of hMPV infection. The body weight for each rat was monitored on a daily basis. At day 5 post-challenge, all rats from each group were euthanized. The lungs and nasal turbinate from each rat were collected for virus isolation and histological evaluation.

Determination of viral titer in lung and nasal turbinate. Nasal turbinates and the right lung from each cotton rat were removed, weighed, and homogenized in 1 ml of phosphate-buffered saline (PBS) solution. The presence of infectious virus was determined by an immunostaining assay in Vero-E6 cells as described previously.

Reverse transcription polymerase chain reaction (RT-PCR) and sequencing. Viral RNA was extracted from each recombinant hMPV mutant, lung or nasal turbinate tissue using an RNeasy mini-kit (Qiagen) following the manufacturer's recommendation. RT-PCR was performed using a One Step RT-PCR kit (Qiagen) with two hMPV F-specific primers, 5'-CGGAATTCATGTCTTGGAAAGTGGT-GATC-3' (forward, SEQ ID NO: 8) and 5'-CCGCTC-GAGCTAATTATGTGGTATGAAGC-3' (reverse, SEQ ID NO: 9). The PCR products were purified and sequenced at The Ohio State University Plant Microbe Genetics Facility to confirm the presence of the designed mutations.

Quantification of viral RNA in lung and nasal turbinate by real-time RT-PCR. Viral RNA in lung and nasal turbinate was quantitated by real-time RT-PCR. Total RNA was extracted from samples using an RNeasy Kit (Qiagen), followed by reverse transcription and real-time PCR. First strand cDNA was synthesized by SuperScriptase III (Invitrogen) using the primer N-P1 (5'-TTATAATACACGTCT-GCGCCC-3' SEQ ID NO: 10), which targets the N gene of hMPV. The N gene was then quantified by real-time PCR using custom Taqman primers and probes (Forward primer, 5'-CACCGCCGGGAAAATCA-3' SEQ ID NO: 11) (Reverse primer: 5'-GCCTTCAGTTGGGAAATTTGG-3' SEQ ID NO: 12) (Reporter; 5'-FAM-ATTTGCAGCAGTCCC-NFQ-3' SEQ ID NO: 13) on a StepOne real-time PCR machine (Applied Biosystems, Foster City, Calif.). PCR reaction and cycling parameters followed the manufacturer's protocol (Invitrogen). TaqMan Fast Universal Master Mix was used for all reactions. For cycling parameters, a holding stage at 95° C. was maintained for 20 seconds prior to cycling, followed by 50 cycles of 95° C. for 1 second for annealing and 60° C. for 20 seconds for extension. Standard curves and StepOne Software v2.1 were used to quantify genomic RNA copies. Viral RNA was expressed as mean log 10 genomic RNA copies/ml±standard deviation.

Detection of antibody by ELISA. 96-well plates were first coated with 50 µl of highly purified hMPV (30 µg/ml, in 50 mM $Na_2CO_3$ buffer, pH 9.6) per well at 4° C. overnight. Subsequently, individual serum samples were tested for hMPV-specific antibody on antigen-coated plates. Serum samples were two-fold serially diluted and added to hMPV-coated wells. After incubation at room temperature for 1 h, the plates were washed five times with phosphate buffered saline (PBS)-Tween (0.05%), followed by incubation with 50 µl of goat anti-mouse IgG horseradish peroxidase (HRP)-conjugated secondary antibodies (Sigma) at a dilution of 1:80,000 for 1 h. Plates were washed and developed with 75 µl of 3,3',5,5'-tetramethylbenzidine (TMB), and the optical density (OD) at 450 nm was determined using an ELISA plate reader. End point titers were determined as the reciprocal of the highest dilution that had an absorbance value greater than the background level (DMEM control). Antibody titers were calculated by the Geometric Mean Titers (GMT).

Plaque reduction virus neutralization assay. The hMPV neutralizing antibody was determined using a plaque reduction neutralization assay. Serum samples from cotton rats were heat inactivated at 56° C. for 30 min, and were subjected to twofold serial dilutions on 96-well-plates. Each serum dilution was mixed with equal volume of OPTI-MEM containing 100 PFU of wild type rhMPV followed by incubation at room temperature for 1 h. The mixture was then transferred to Vero-E6 cells in 96-well-plates. After 1 h incubation at 37° C., cells were overlaid with 0.75% methylcellulose in OPTI-MEM medium and incubated at 37° C. for 4 days followed by immuno-staining with monoclonal antibody against hMPV N protein as described above. Neutralizing antibody titers were expressed as the reciprocal of the serum dilution that resulted in 50% reduction in plaque numbers as compared to normal cotton rat serum control. Each serum was tested in duplicate.

Histology. Right lung from each cotton rat was preserved in 4% (v/v) phosphate-buffered paraformaldehyde. Fixed tissues were embedded in paraffin, sectioned at 5 microns, and stained with hematoxylin-eosin (HE) for the examination of histological changes by light microscopy. Histopathological changes were scored including the extent of inflammation (focal or diffuse), the pattern of inflammation (peribronchilolar, perivascular, interstitial, alveolar), and the nature of the cells in the infiltrate (neutrophils, eosinophils, lymphocytes, macrophages). Deparaffinized sections were also stained with monoclonal antibody against hMPV matrix protein (Virostat, Portland, Me.) to determine the distribution of viral antigen. The histological slides were examined independently by three pathologists.

Structure modeling of F protein. The structure prediction of the hMPV F protein was performed using Modeller 9.0 based on the prefusion crystal structure of RSV F protein (PDB ID: 4JHW) as a template.

Statistical analysis. All experiments were repeated three to five times. Quantitative analysis was performed by either densitometric scanning of autoradiographs or by using a phosphorimager (GE Healthcare, Typhoon) and ImageQuant TL software (GE Healthcare, Piscataway, N.J.). Statistical analysis was performed by one-way multiple comparisons using SPSS 8.0 statistical analysis software (SPSS Inc., Chicago, Ill.). A P value of <0.05 was considered statistically significant.

Figure 1B:
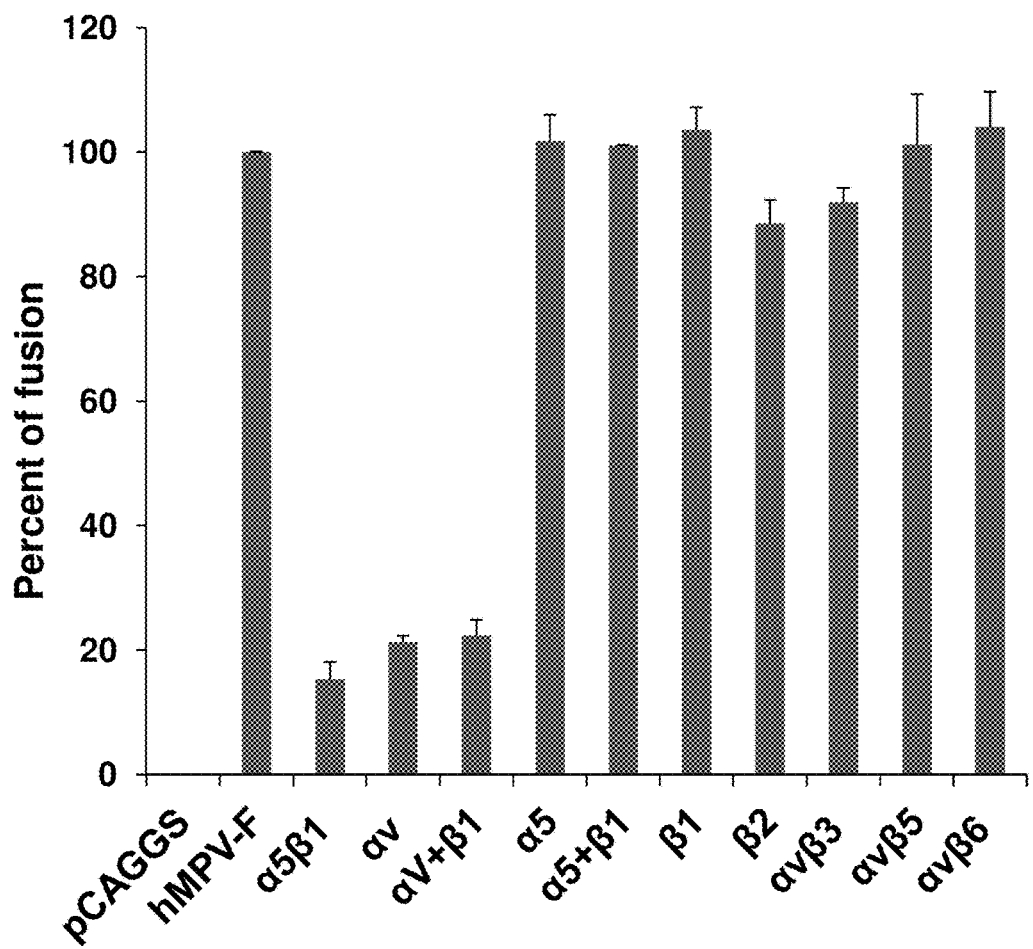
FIG. 1B: Content mixing fusion assay in the presence of integrin antibodies. Vero E6 cells were co-transfected with 2 μg of pCAGGS-F and a reporter gene plasmid (pGINT7). At 24 h post-transfection, the cells were detached with trypsin and mixed with equal numbers of BHKT7 cells which express T7 RNA polymerase. Then, the cells were incubated with 2 ml of OPTI-MEM containing 5 μg/ml of selected integrin antibody and 0.2 μg/ml of TPCK-trypsin for 12 h. The cells were lysed and mixed with equal amount of β-galactosidase substrate chlorophenol red-β-D-galactopyranoside (16 mM). The extent of fusion was quantitated by microplate spectrophotometer at the absorbance of 570 nm. Percent of fusion for each antibody treatment was normalized to the fusion of pCAGGS-F in the absence of integrin antibody. Data shown are averages for three independent experiments.

Example 2

α5β1 and αv Integrin-Specific Antibodies Inhibit hMPV F-Induced Cell-Cell Fusion Previously, it has been shown that hMPV engages αvβ1 integrin to mediate virus infection, suggesting that integrins might serve as functional receptors for hMPV. However, it is not known whether integrins are involved in hMPV F-mediated cell-cell fusion. To address this question, it was first determined whether integrin-specific antibodies can inhibit cell-cell fusion triggered by hMPV F protein. Vero E6 cells were transfected with pCAGGS-F, followed by incubation with specific anti-integrin antibodies, and fusion was determined by assaying for syncytium formation. As shown in FIG. 1A, incubation with an antibody specific for α5β1 led to a significant reduction in syncytium formation in comparison with the no antibody control. However, hMPV F-transfected cells treated with antibodies against αvβ3, αvβ5, and αvβ6 subtypes displayed syncytia similar to those of the untreated control. Incubation with antibodies against either the α5 subunit or β1 subunit alone did not have a significant effect on syncytium formation. Similarly, the combination of anti-β1 and anti-α5 antibodies as well as antibody against the β2 subunit did not exhibit any inhibitory effect. In contrast, incubation of hMPV F-transfected cells with an antibody against αv and the combination of antibodies against αv and β1 subunits notably diminished the formation of syncytia. Subsequently, the extent of cell-cell fusion was quantified by the content-mixing fusion assay. As shown in FIG. 1B, the fusion of hMPV F-transfected cells was inhibited by approximately 80% in the presence of anti-α5β1 or anti-αv antibody. In contrast, none of the other tested integrin antibodies had a significant effect on fusion in comparison with untreated cells (P>0.05). Taken together, these results demonstrated that anti-α5β1 and anti-αv antibodies specifically inhibited cell-cell fusion triggered by the hMPV F protein.

Example 3

Figure 2A:
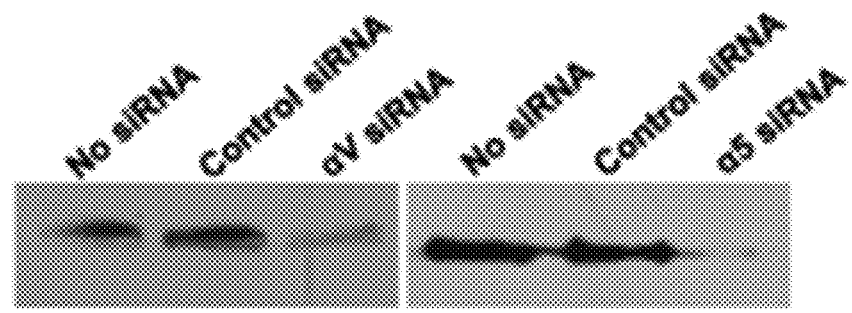
FIGS. 2A-2C: siRNAs targeting $\alpha 5$ and $\alpha V$ backed cell-cell fusion triggered by hMPV F.
Figure 2B:
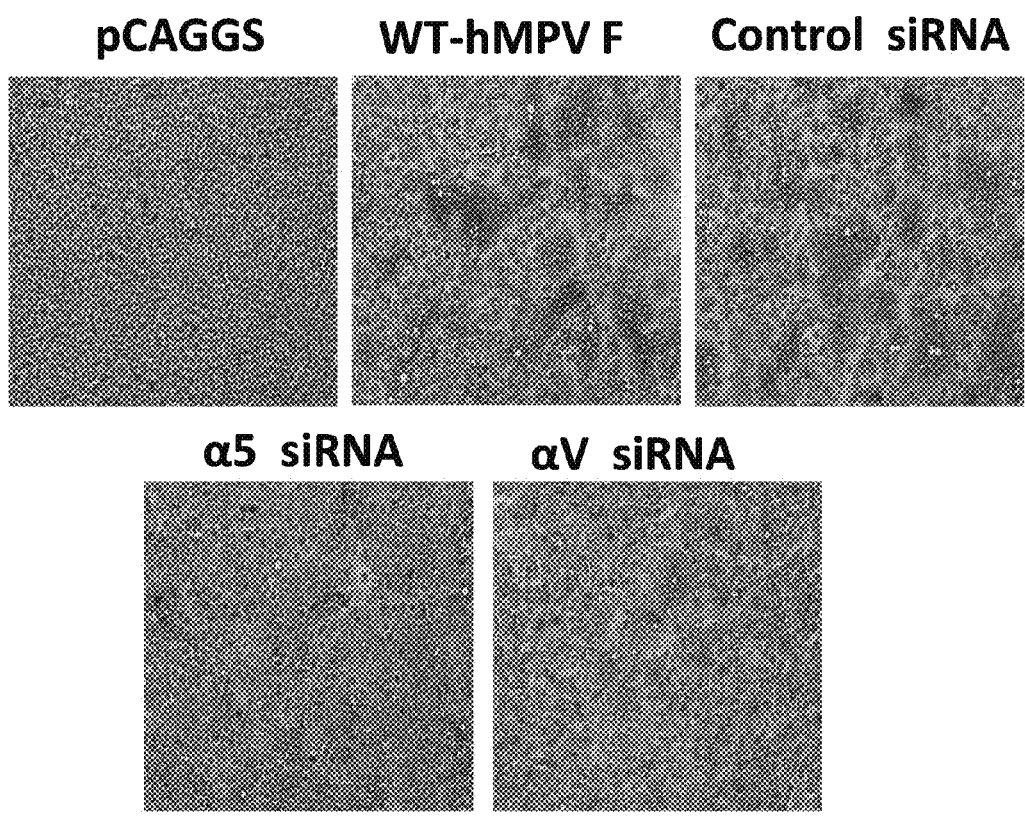
Figure 2C:
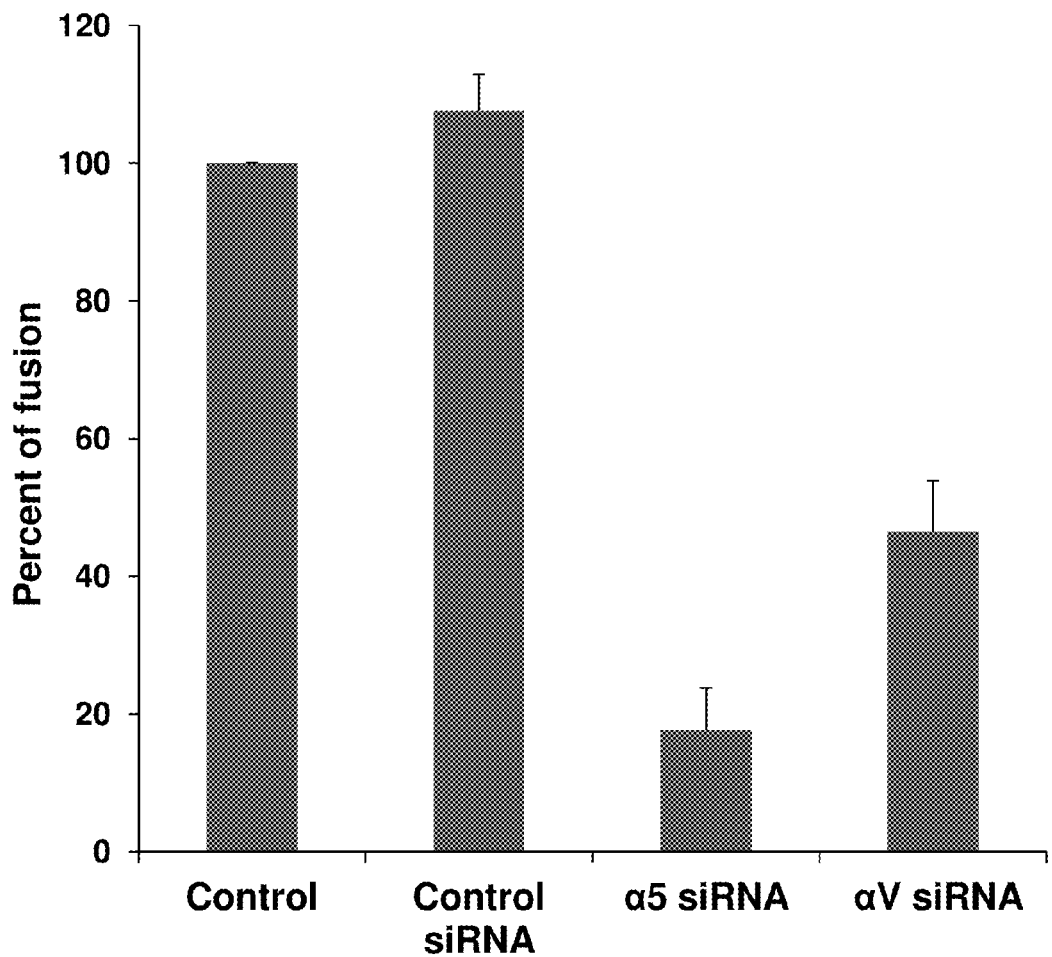

Down-Regulating the Expression of α5 or αv Subunit Diminished hMPV F-Triggered Cell-Cell Fusion To further determine the role of α5β1 and αv integrins in cell-cell fusion, the α5 or αv integrins were knocked down using siRNA targeting these two subunits. Vero E6 cells were first transfected with α5 or αv-targeting siRNAs, which reduced the expression of α5 or αv subunit on the cell surface by approximately 85% (FIG. 2A). Subsequently, the siRNA-treated cells were transfected with pCAGGS-F, and syncytium formation was examined. As shown in FIG. 2B, fusion was significantly reduced in cells transfected with siRNAs targeting α5 or αv integrin, but not in cells transfected with control siRNA. Further quantitative analysis (FIG. 2C) demonstrated that α5 and αv siRNA reduced fusion activity by approximately 80% and 60%, respectively. Down-regulating the expression of α5 or αv subunit diminished hMPV F-triggered cell-cell fusion.

Example 4

Figure 3:
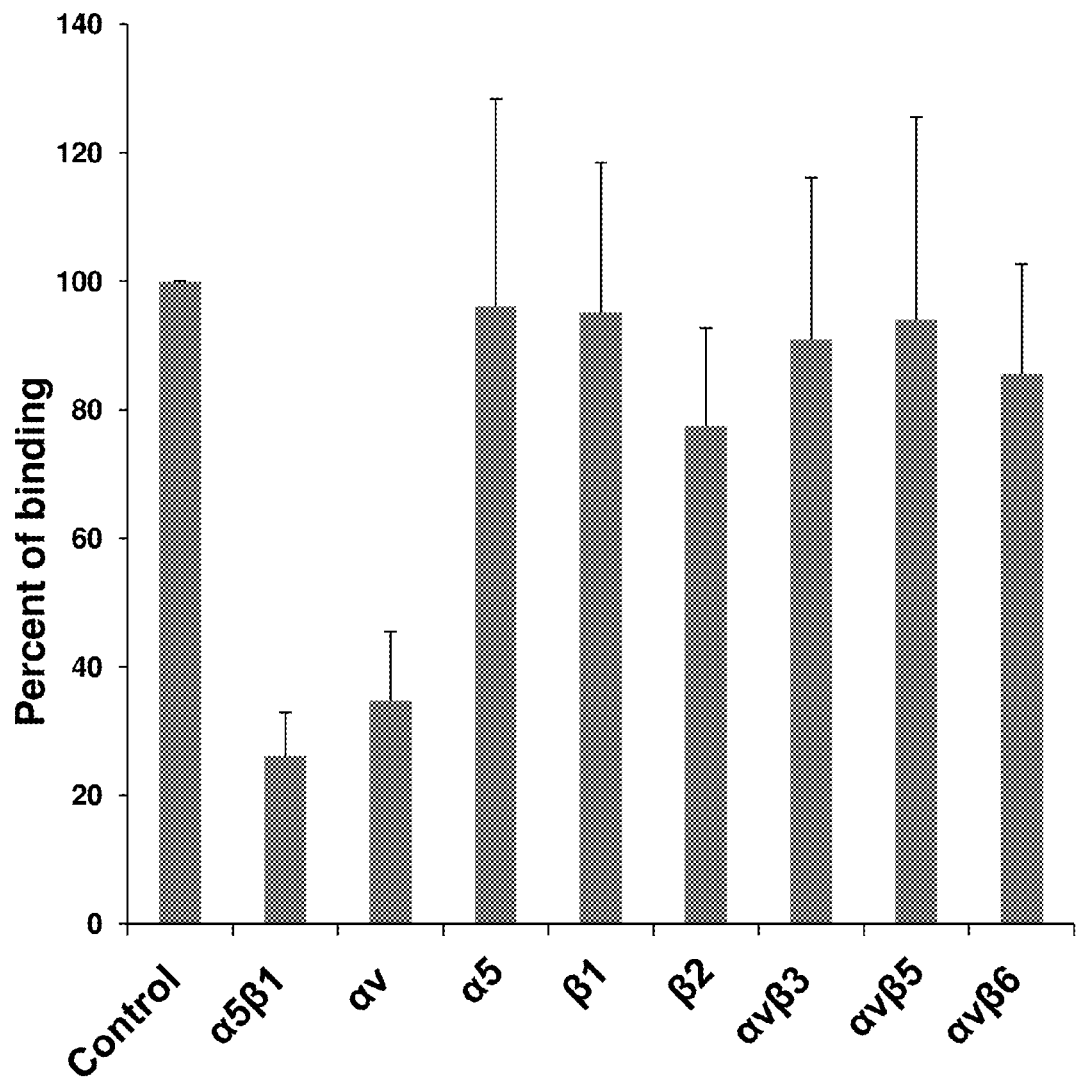
FIG. 3: Integrin $\alpha 5\beta 1$ and $\alpha v$ antibodies inhibited hMPV infectivity in host cells. Confluent monolayers of LLC-MK2 cells in 96-well plates were pretreated with each integrin antibody (20 μg/ml) at 37° C. for 1 h. Then, the cells were shifted to a 4° C. incubator for 30 min. The cells were incubated with hMPV at MOI of 100 PFU/well. After incubation on ice for 1 h (shake every 15 min), the inoculum was removed, and the cells were washed with cold OPTI-MEM for 3 times. The infected cells were then incubated with fresh DMEM at 37° C. and 5% CO2. After 24 h, the binding and infectivity was determined by counting immunostaining spots. The percent of infectivity for each antibody treatment was normalized by the infectivity of hMPV without antibody treatment. Data shown are averages for three independent experiments.

Specific Anti-α5β1 and αv Antibodies Inhibited hMPV Infectivity in Vero-E6 Cells The effect of various anti-integrin antibodies on hMPV infection in Vero E6 cells was then investigated. Vero E6 cells were incubated with different anti-integrin antibodies at 37° C. for 1 h prior to hMPV infection. Cells were infected with hMPV at an MOI of 100 per well. After incubation on ice for 1 h, the unbound viruses were removed by washing with OPTI-MEM three times. At 24 h post-infection, the amount of hMPV bound to Vero-E6 cells was determined by immunostaining as described above in Example 13. As shown in FIG. 3, antibodies specific for α5β1 and αv integrins inhibited 75% and 85% of hMPV infectivity in Vero-E6 cells, respectively, whereas other integrin antibodies, including α5, β1, β2, αvβ3, αvβ5, and αvβ6, had no significant effect on hMPV infectivity. These results are consistent with the finding that antibodies specific for α5β1 and αv integrins efficiently inhibited cell-cell fusion triggered by hMPV F protein.

Example 5

α5β1 Integrin Expressing Cells Enhanced Viral Infectivity

Figure 4A:
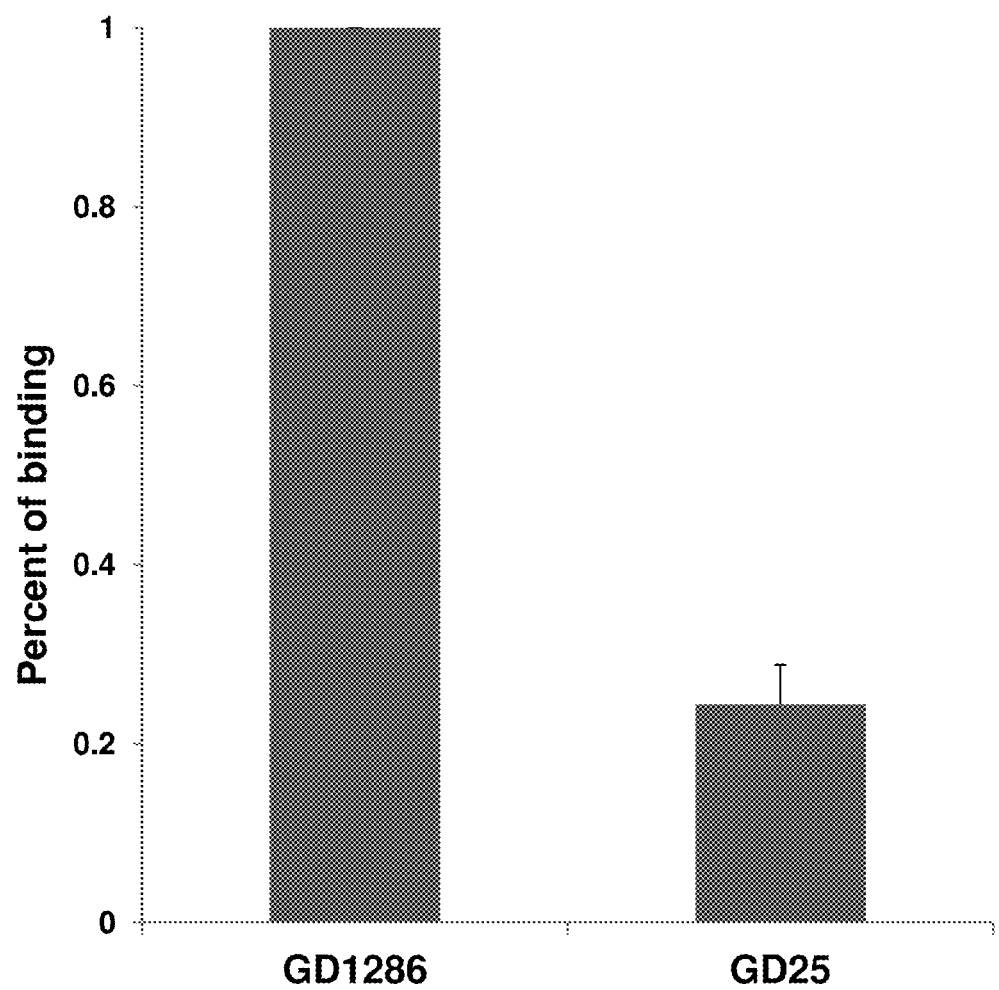
FIGS. 4A-4B: Infectivity of hMPV in an integrin-deficient cell line.
Figure 4B:
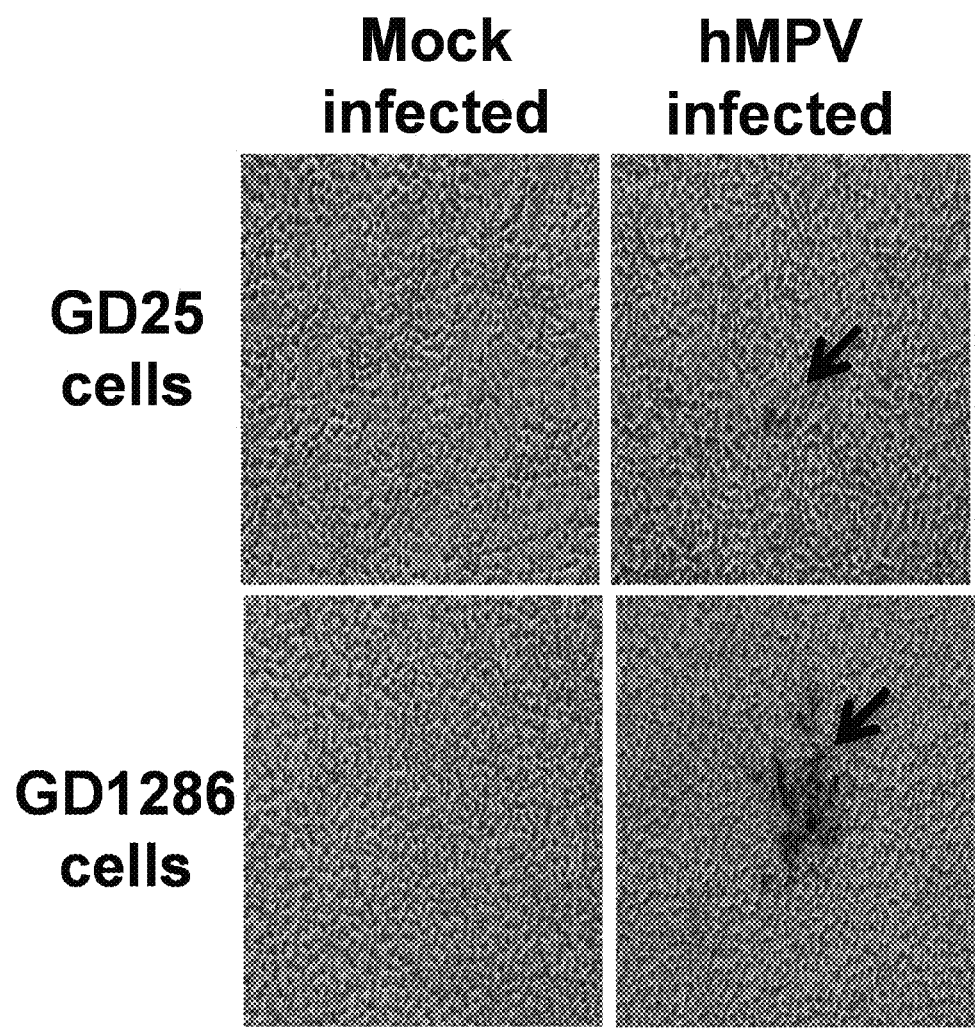

To further determine the role of α5β1 integrin in viral binding and infectivity, cell lines that were defective in integrin or stably-expressing integrin receptors were used. Specifically, the binding and infectivity of hMPV in the mouse fibroblast cell line GD25 was examined, which lacks expression of the β1 family of integrin heterodimers and GD1286 cell that constitutively express α5β1 integrin receptor. As shown in FIG. 4A, the infectivity of hMPV in GD1286 cells was approximately 4 times higher than that of GD25, consistent with the idea that the expression of α5β1 integrin significantly increases the binding and infectivity of hMPV to host cells. The size of immunospots formed in GD1286 cell monolayers was much larger than that in GD25 (FIG. 4B), suggesting that α5β1 integrin may also play a role in cell-to-cell spread.

Example 6

Mutations in the RGD Motif of the hMPV F Protein Impair Fusion Activity

The above results demonstrate that α5β1 and αv integrins play essential roles in hMPV F-triggered cell-cell fusion, as well as viral binding and infectivity. Consistent with this, a putative integrin binding motif ($^{329}$RGD$^{331}$) is present in the F proteins of all known hMPV strains. The corresponding motif in the F protein of aMPV subtype C strain is $^{329}$RSD$^{331}$. To determine the role of the RGD motif in hMPV cell-cell fusion, an extensive mutagenesis analysis of this motif has been performed. As summarized in Table 1, three classes of substitutions were generated: (i) alanine substitutions, including R329A, G330A, and D331A; (ii) mutations that conserve charge, namely, R329K and D331E; and (iii) mutations that introduce a charge change, including R329D and D331R. In addition, a G330S mutation was introduced into the hMPV F protein to mimic the aMPV F protein.

Figure 5A:
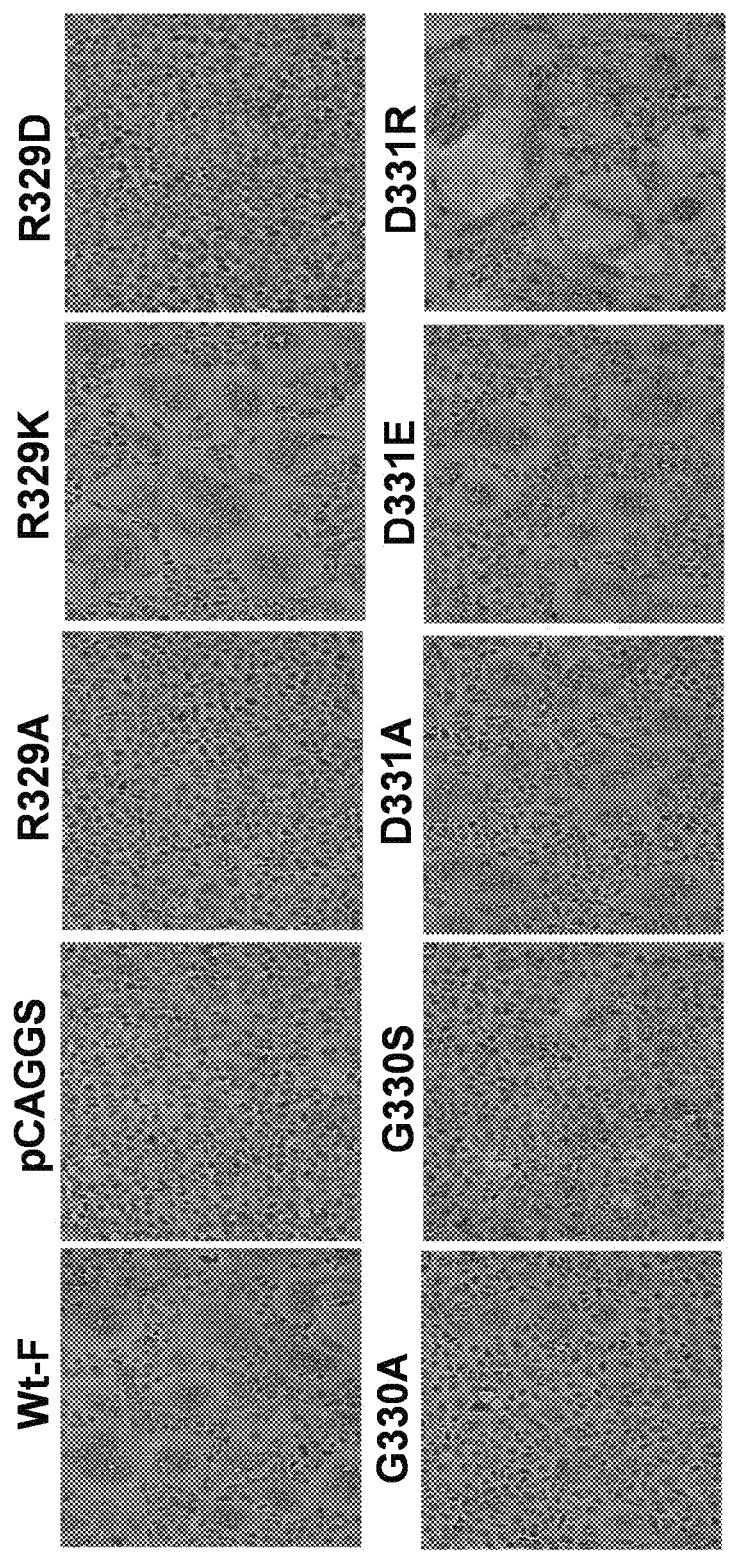
FIGS. 5A-5C: Effects of mutations to RGD motif on cell-cell fusion triggered by hMPV F protein.
Figure 5B:
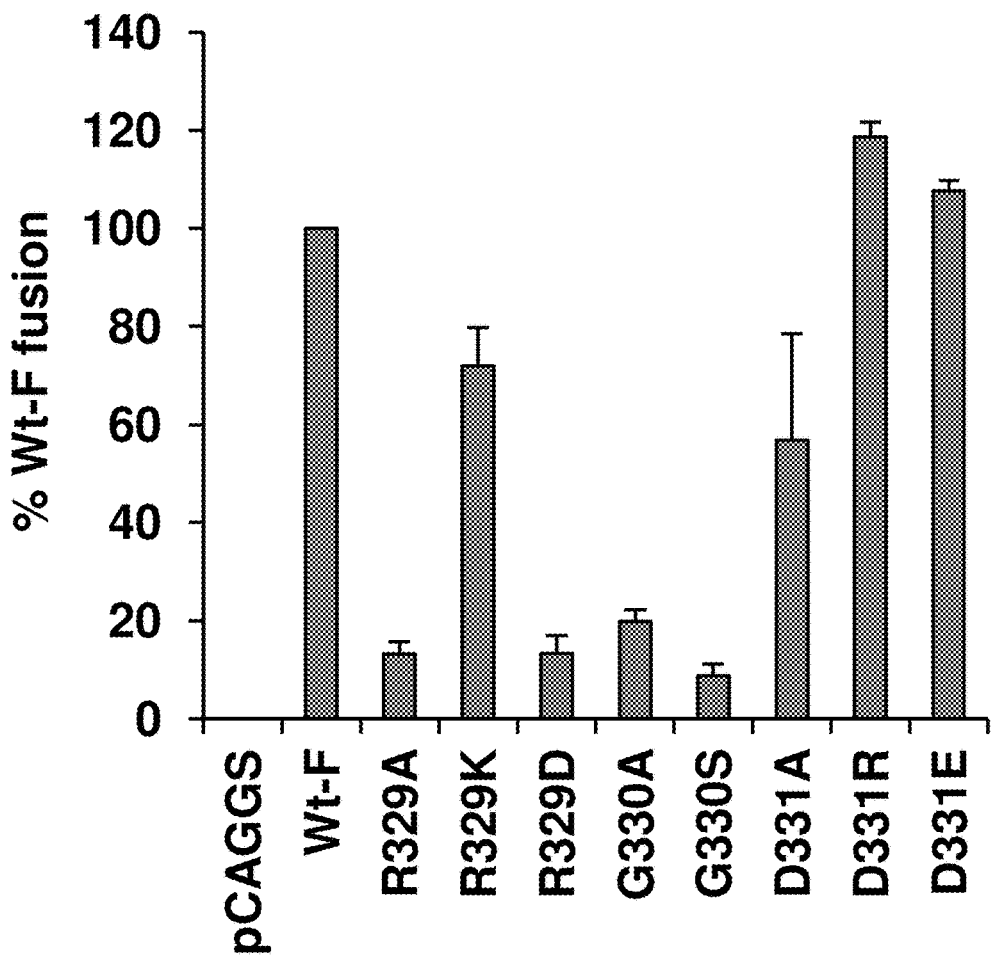
Figure 5C:
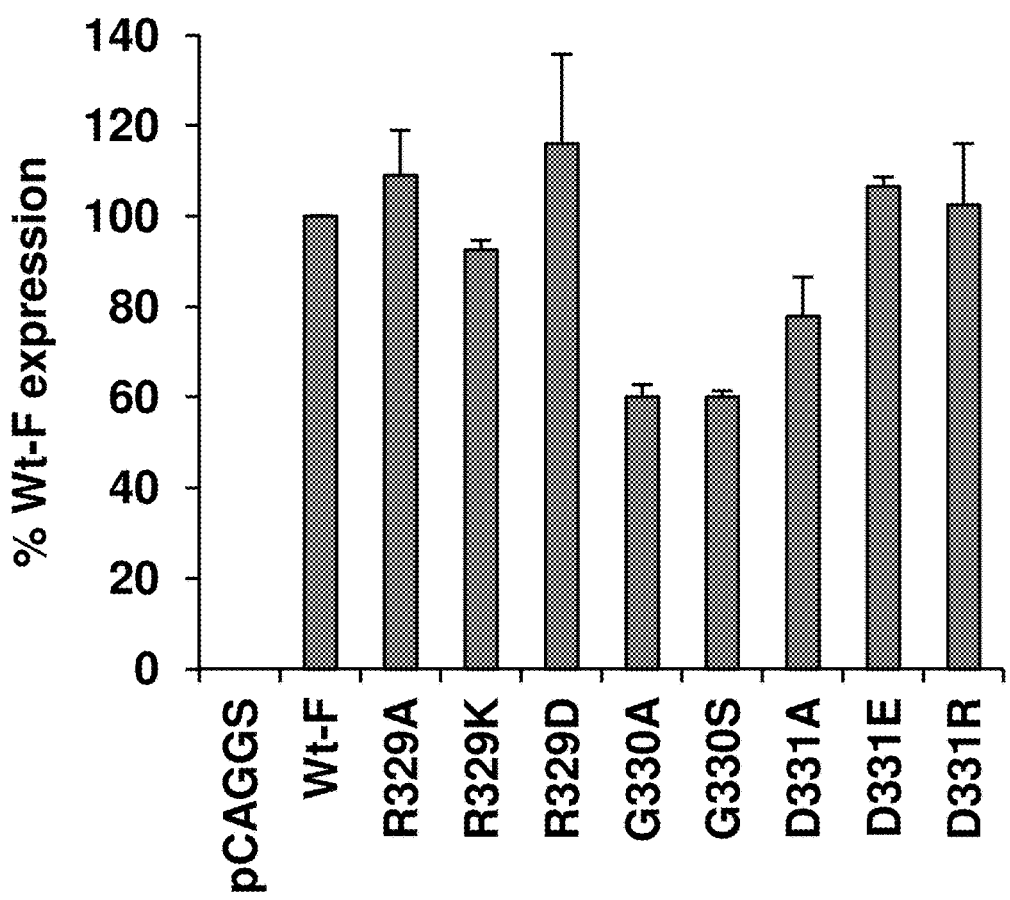

All F mutants were transfected into Vero E6 cells and their cell surface expression and fusion activities were evaluated. As shown in FIG. 5C, all F mutants were efficiently expressed at cell surface as determined by FACS. R329A and G330A significantly decreased the extent of syncytia formation as compared with wt hMPV F, whereas R329K and D331A slightly diminished the size of syncytia (FIG. 5A). However, R329D and G330S mutations significantly impaired fusion activity; no syncytium formation was observed with these two F mutants until 48 h post-transfection. The D331E and D331R mutants, especially the latter, were able to form syncytia that were larger than that of wt hMPV F protein.

TABLE 1

Summary of the mutations in RGD motif

| Mutant | Rationale | Fusion | Virus recovery | Viral titer $^A$ | Replication in LLC-MK2 cells $^B$ | Replication in cotton rats $^C$ |
|---|---|---|---|---|---|---|
| WT-F | / | 100% | Recovered | $2.5 \times 10^6$ | 100% | WT |
| R329A | Change to neutral | 13% | Lethal | NA | NA | NA |
| R329K | Maintain charge | 72% | Recovered | $1.2 \times 10^6$ | Attenuated | Attenuated |
| R329D | Change to negative charge | 13% | Lethal | NA | NA | NA |
| G330A | Maintain size | 20% | Recovered | $3.0 \times 10^2$ | Attenuated | NA |
| G330S | Mimic RSD in aMPV-C F | 9% | Unstable | NA | NA | NA |
| D331A | Change to neutral | 58% | Recovered | $1.0 \times 10^6$ | Attenuated | Attenuated |
| D331E | Maintain charge | 118% | Recovered | $1.8 \times 10^6$ | WT | WT |
| D331R | Change to positive charge | 107% | Recovered | $4.0 \times 10^6$ | WT | WT |

$^A$ Viral titer was determined by immunostaining assay; NA: non-applicable
$^B$ Attenuation was judged by plaque size, infectivity, and growth curve; WT: wild type level of replication cell culture
$^C$ Attenuation was judged by viral replication in nasal turbinate and lung, and histology; WT: wild type level of replication in cotton rats The extent of fusion was also quantified in a content mixing fusion assay. As shown in FIG. 5B, R329A, R329D, G330A, and G330S mutants decreased the level of fusion to less than 20% of wt hMPV F protein, while R329K and D331A decreased fusion activity to 50-80% of wt. Consistent with the results from staining, the D331R and D331E mutants exhibited even higher fusion activity compared to wt F. Taken together, these data showed that: (i) alanine substitution for the first two amino acid residues (R329 and G330) in the RGD motif dramatically reduce fusion activity, whereas an alanine substitution for the third amino acid residue (D331) resulted in less dramatic decrease in fusion; (ii) maintenance of the positive charge at amino acid position 329 is essential for fusion; (iii) substitution of the RGD motif found in hMPV F protein with that of the RSD motif found in aMPV F protein significantly impaired the fusion activity; and (iv) replacement of D331 with a positively or negatively-charged residue did not affect fusion. These results showed that amino acid residues R329 and G330 within the RGD motif are essential for fusion activity, whereas the identity of the amino acid residue at position 331 is less important.

Example 7

Mutations in the RGD Motif of hMPV F Protein Impaired the Cell Binding Activity

Figure 6:
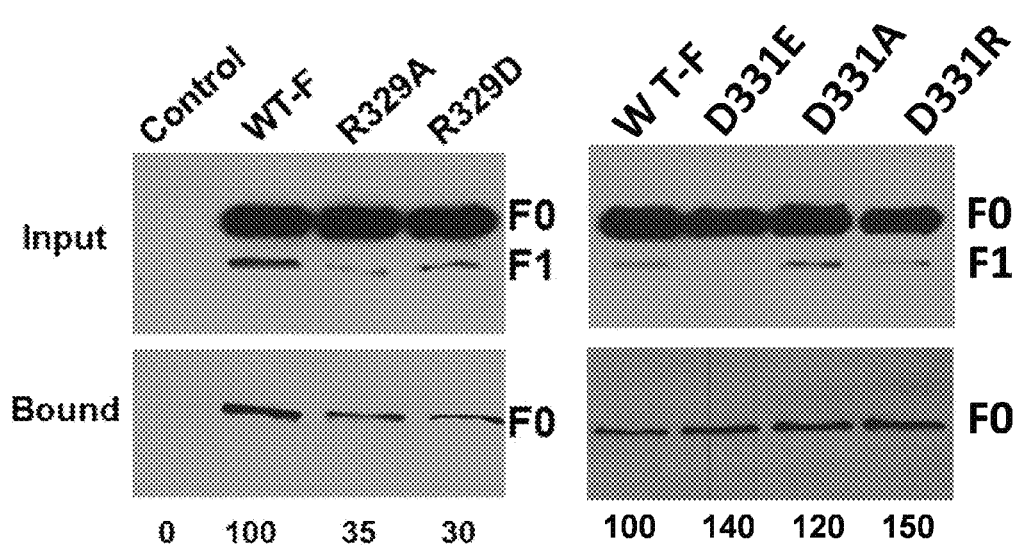
FIG. 6: Effect of mutations to RGD motif on the binding of F protein to host cells. To determine whether a soluble hMPV F protein is capable of binding to host cells, LLC-MK2 cells were incubated with sF protein, and the amount of sF protein binding to cells was detected by Western blot and quantitated by densitometry. sF mutants R329A, R329D had defects in binding to host cells whereas sF mutants D331A, D331E and D331R did not significantly alter the binding affinity.

If RGD motif is indeed essential for recognition of integrin receptor and fusion promotion, mutations to this motif would affect the binding of sF protein to permissive cells. To facilitate functional studies of the hMPV F protein, the inventors produced an anchorless soluble F protein ectodomain by removing the transmembrane and cytoplasmic domains. A 6-His tag (SEQ ID NO: 5) was linked to the C terminus to facilitate protein purification and detection. As shown in FIG. 6, both the precursor, F0, and the cleaved F1 protein were detected in the cell lysate and the medium. However, the majority of sF protein retained its uncleaved form. This result shows that sF1 protein is not only efficiently expressed in cells, but also secreted into cell culture medium. As shown in FIG. 6, all the sF mutants within RGD motif were efficiently expressed and purified. To determine whether a soluble hMPV F protein is capable of binding to host cells, LLC-MK2 cells were incubated with sF protein, and the amount of sF protein binding to cells was detected by Western blot and quantitated by densitometry. As shown in FIG. 6, sF mutants R329A, R329D had remarkable defects in binding to host cells whereas sF mutants D331A, D331E and D331R did not significantly alter the binding affinity. Thus, these results showed that RGD motif in hMPV F essential for binding for host cells.

Example 8

Recovery of rhMPV Carrying Mutations in the RGD Motif of F Protein

Figure 7:
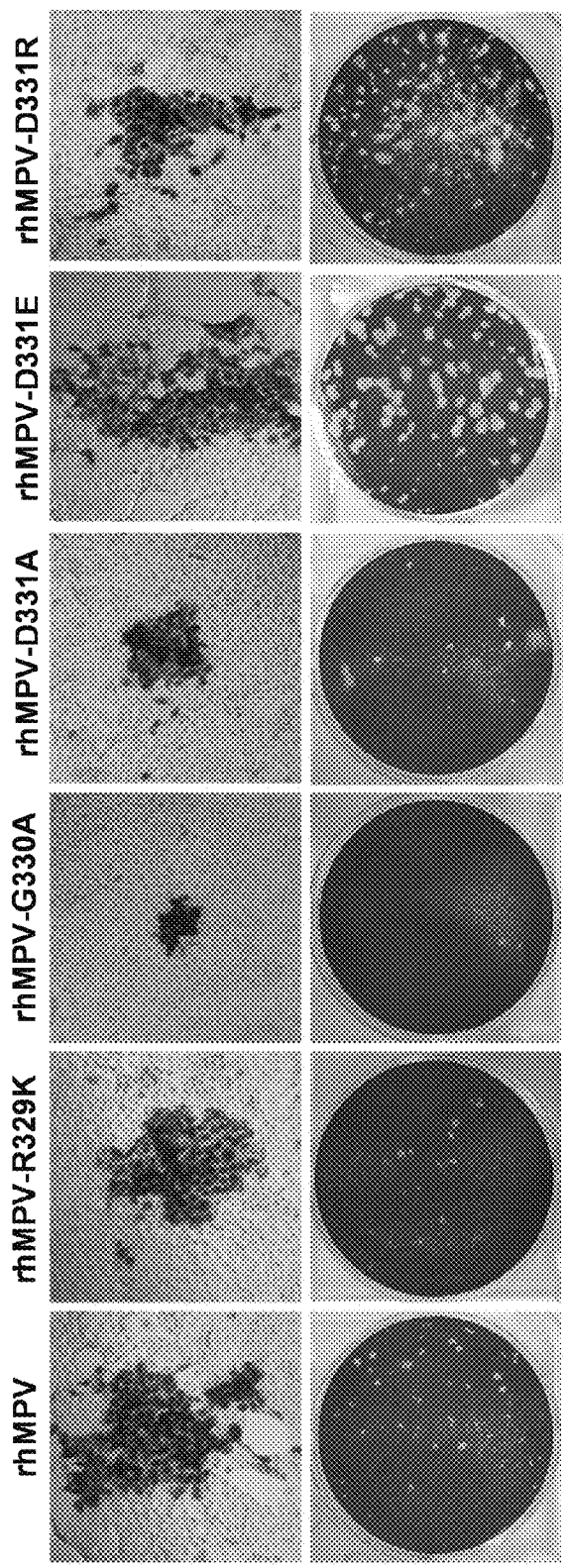
FIG. 7: Recovery of recombinant hMPVs carrying mutations in RGD motif. Top Row) Immunostaining spots formed by recombinant hMPVs. LLC-MK2 cells were infected with recombinant hMPV mutants and incubated at 37° C. for 1 h. At day 4 post-infection, the supernatant was removed and cells were fixed. The cells were then labeled with an anti-hMPV N protein primary monoclonal antibody, followed by incubation with horseradish peroxidase (HRP)-labeled rabbit anti-mouse secondary antibody. After incubation with AEC substrate chromogen, positive cells with immunostaining spots were visualized under the microscope. Bottom Row) Plaque morphology of recombinant hMPVs. An agarose overlay plaque assay was performed in monolayer Vero E6 cells. Viral plaques were developed at day 7 post-infection.

To evaluate the role of the RGD motif in viral infectivity and pathogenesis, recombinant hMPV (rhMPV) carrying mutations in the RGD motif of the F protein were constructed and recovered. Each of the above mutations was introduced into an infectious cDNA clone of hMPV NL/1/00 and recombinant hMPV carrying individual RGD mutations were recovered. The successful recovery of recombinant viruses was initially identified by an immunostaining assay using a monoclonal antibody against hMPV N protein and further confirmed by a direct agarose overlay plaque assay. Using these approaches, rhMPV carrying R329K, G330A, G330S, D331A, D331R, and D331E mutations in RGD motif were recovered (FIG. 7). However, no recombinant viruses with the R329A and R329D mutations were recovered after multiple attempts, showing that these mutations are lethal to hMPV. As shown above, these F mutants had retained less than 20% of the fusion activity of wild type F (FIG. 5). As shown in FIG. 7 (upper panel), recombinant rhMPV-G330A, D331A, and R329K formed much smaller immuno-spots at day 7 post-infection whereas recombinant rhMPV-D331R and D331E formed immuno-spots that were comparable to rhMPV. The ability of these recombinant viruses to form plaques in Vero-E6 cells was determined by an agarose overlay plaque assay (FIG. 7, lower panel). After 7 days of incubation, the average plaque size for rhMPV-R329K and D331A were 0.91 mm and 0.75 mm in diameter, respectively, which were significantly smaller than that of rhMPV (1.10 mm). In contrast, rhMPV-D331E and D331R formed plaques which were significantly larger than that of rhMPV. rhMPV-G330A was not able to form plaques although it can form immuno-spots by an immunostaining assay (FIG. 7). Finally, the entire F gene of each recombinant virus was amplified by RT-PCR and sequenced. All recombinant viruses contained the desired mutation in RGD motif except for rhMPV-G330S. Subsequently, all passages of rhMPV-G330S were sequenced, and it was found that it had reverted back to wild type after the third passage in Vero-E6 cells. Since rhMPV-G330S is not genetically stable, this mutant was not included in subsequent studies.

Example 9

Figure 8:
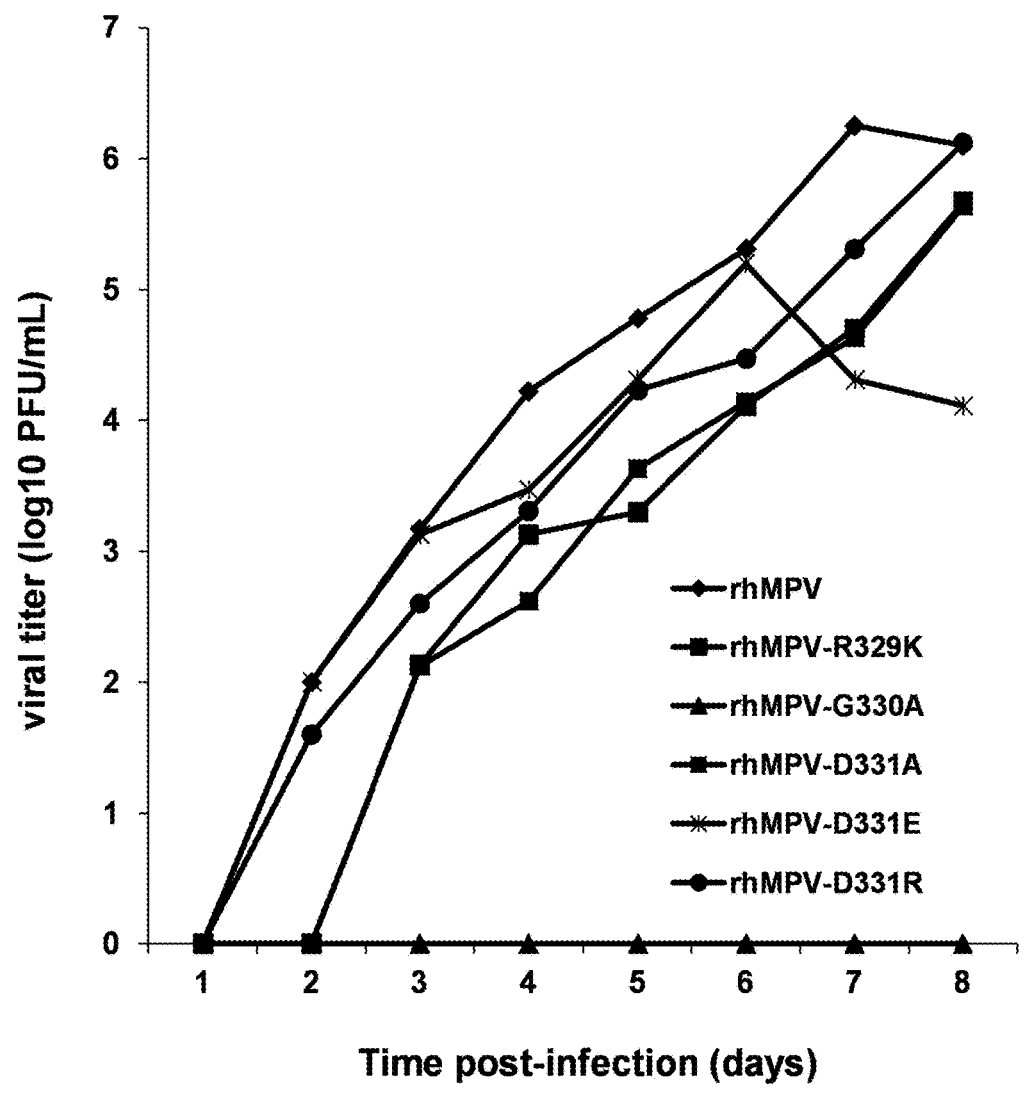

Recombinant hMPV Carrying Single Mutations in the RGD Motif Result in Defects in Viral Replication The replication kinetics of these hMPV mutants were determined in LLC-MK2 cells. LLC-MK2 cells were infected with each recombinant virus at an MOI of 0.01. At the indicated time points, the amount of virus in the supernatant was determined by immunostaining. As shown in FIG. 8, significant release of infectious virus particles was detected by day 2 post-infection for rhMPV, rhMPV-D331E, and D331R, while the first release of rhMPV-R329K and D331A was observed only at day 3 post-infection. The release of rhMPV-G330A was not detected during the entire 8-day period. Overall, the growth curves of recombinant rhMPV-D331R and D331E were not significantly different from rhMPV (P>0.05). In contrast, recombinants rhMPV-R329K and D331A had significant defects in viral replication as compared to that of rhMPV (P>0.05). Since rhMPV-G330A was not detectable in the supernatant, this virus was harvested at day 14 post-infection by three freeze-thaw cycles followed by low speed centrifugation. A low viral titer ($10^2$ PFU/ml) was detected by immunostaining (Table 1). FIG. 9 shows the cytopathic effects (CPE) caused by each recombinant viruses. Recombinants rhMPV-R329K and D331A exhibited delayed CPE compared to rhMPV. However, CPE caused by rhMPV-D331E was earlier than rhMPV. Collectively, these results are consistent with rhMPV-R329K, G330A, and D331A exhibiting defects in their viral replication kinetics whereas rhMPV-D331R and D331E demonstrated wild type replication.

Example 10

Infectivity of rhMPV Mutants in a Cotton Rat Model

To determine whether rhMPV carrying mutations in RGD motif were attenuated in vivo, all recombinant viruses were inoculated into cotton rats and viral replication and pathogenesis were examined. Neither wt nor mutant rhMPV caused any detectable clinical symptoms of respiratory tract infection in cotton rats. At day 4 post-infection, cotton rats from each group were sacrificed, viral replication in nasal turbinates and lungs were determined, and pulmonary histology was examined. Wt rhMPV replicated efficiently in the nasal turbinate and lungs of all five cotton rats (Table 2). Average viral titers of 105.19 and 104.08 were found in the nasal turbinates and lungs, respectively. Recombinant rhMPV-D331E and D331R replicated as efficiently as rhMPV in cotton rats, producing similar titers in both the nasal turbinates and the lung. For the rhMPV-R329K group, only 1 out of 5 cotton rats had detectable infectious virus in the lung with a titer of 104.16 and 2 out of 5 rats had infectious virus in the nasal turbinates with an average titer of 102.87. For the rhMPV-D331A group, only 2 out of 5 cotton rats had infectious virus in the lungs with an average titer of 102.1, although all 5 animals had infectious virus in the nasal turbinates with an average titer comparable to wild-type rhMPV.

Figure 11:
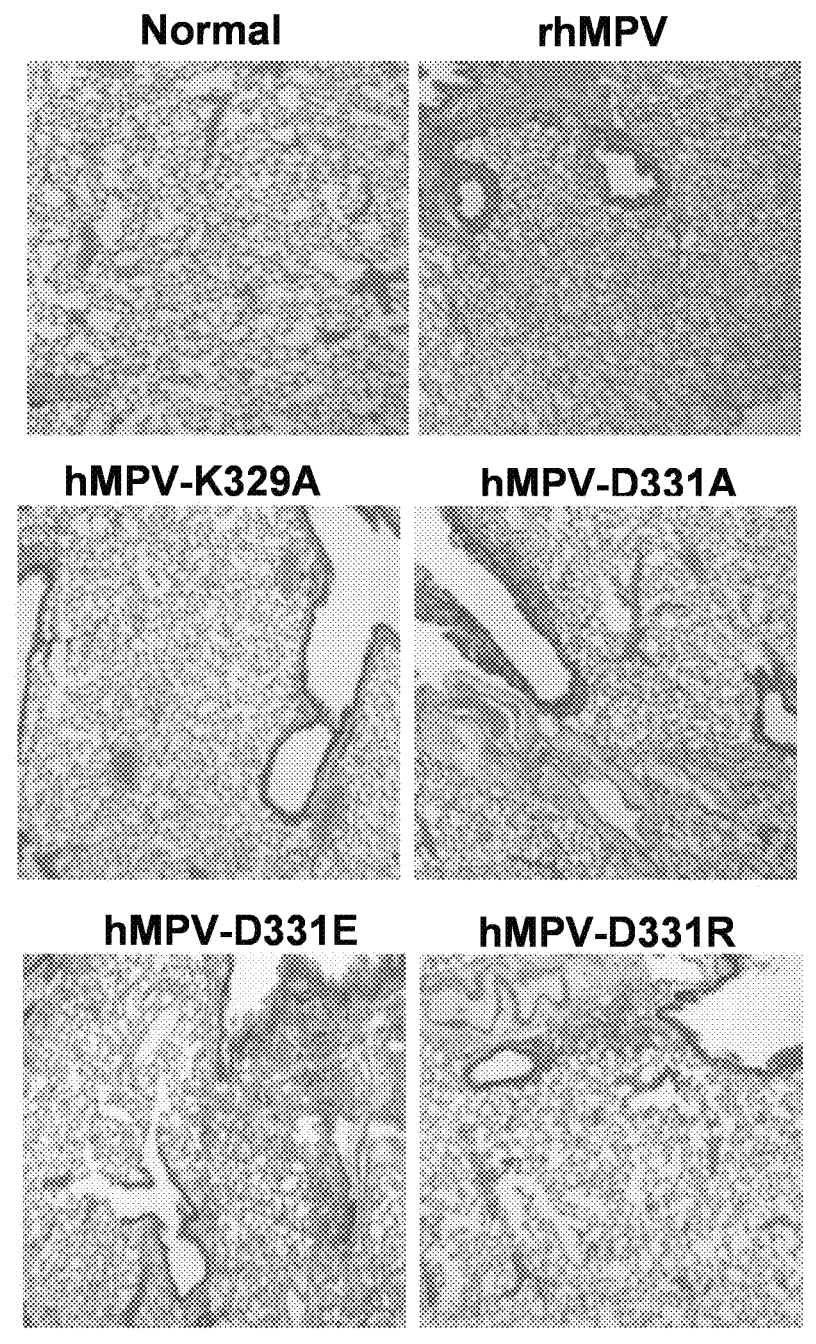

Pulmonary histology showed that rhMPV caused moderate histologic changes including interstitial pneumonia, peribronchial lymphoplasmocytic infiltrates, mononuclear cell infiltrate, and edematous thickening of the bronchial submucosa (FIG. 11). Recombinant rhMPV-D331E and D331R caused less interstitial pneumonia but had significantly increased peribronchial and perivascular inflammation. In contrast, rhMPV-R329K and D331A caused no to mild pulmonary histologic changes.

Figure 12:
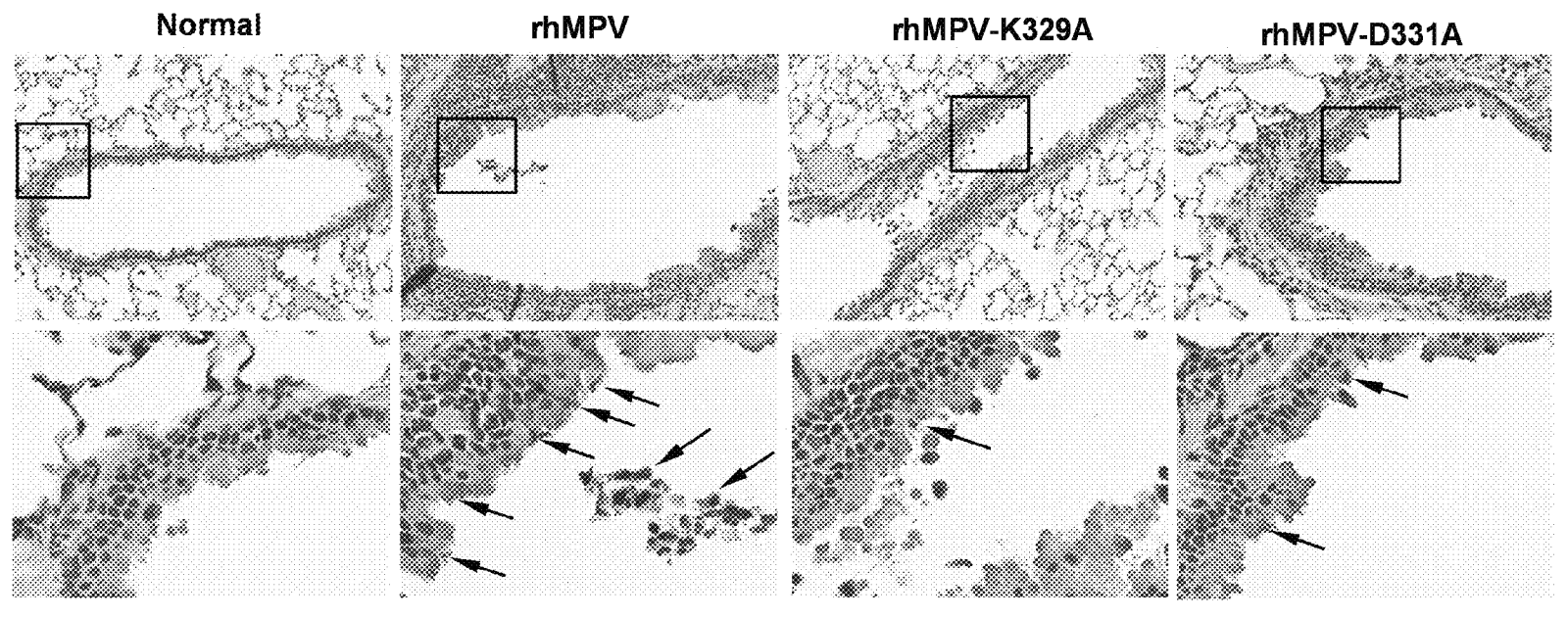

Immunohistobiochemistry analysis found that rhMPV deposited a large amount of viral antigen in epithelial cells in lung tissues whereas significantly less viral antigen was found in the lungs of rhMPV-D331A and R329K infected animals (FIG. 12). Viral antigen expression of rhMPV-D331E and D331R in lung epithelial cells was similar to that of wild-type hMPV. Taken together, these results confirm that rhMPV-D331E and D331R replicated as efficiently as rhMPV, but that rhMPV-R329K and D331A had significant defects in viral replication in cotton rats. These results also showed that rhMPV-R329R and D331A are attenuated both in vitro and in vivo.

Example 11

Immunogenicity of rhMPV-R329K and D331A in Cotton Rats

Figure 13:
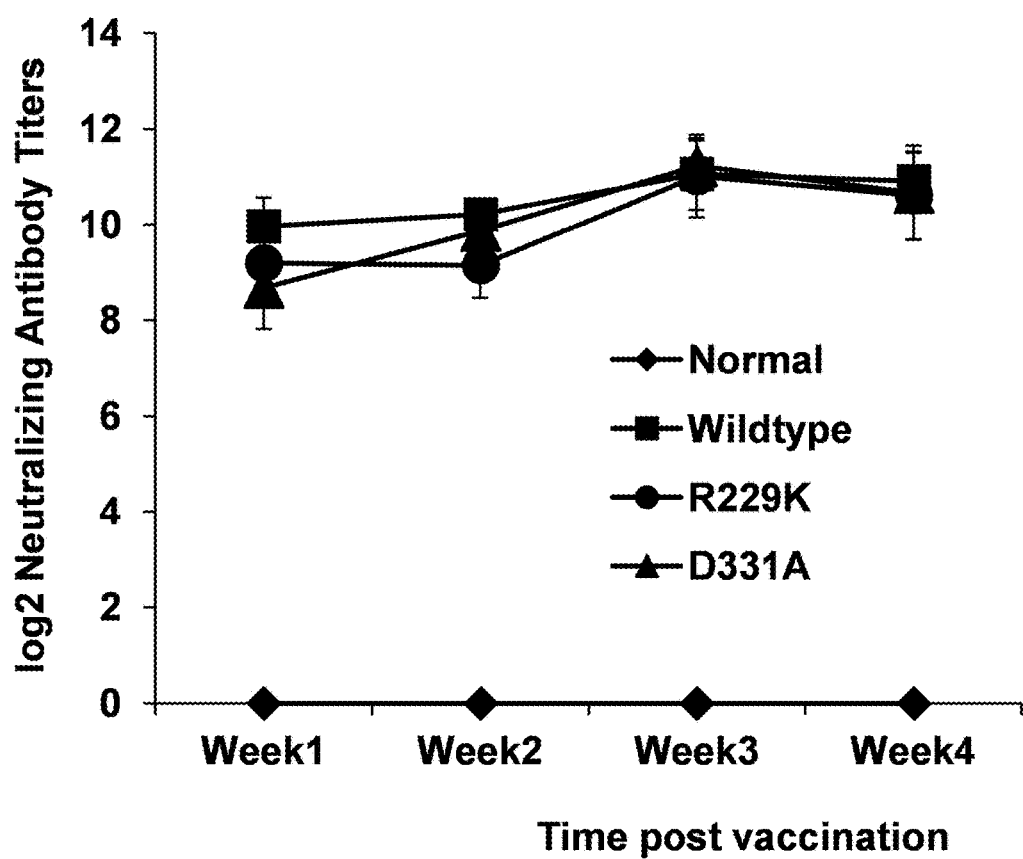
FIG. 13: Lung histobiochemistry of recombinant hMPVs. Lung tissues were fixed in 4% (v/v) phosphate-buffered paraformaldehyde. Deparaffinized sections were stained with monoclonal antibody against hMPV matrix protein (Virostat, Portland, Me.) to determine the distribution of viral antigen.
Figure 14A:
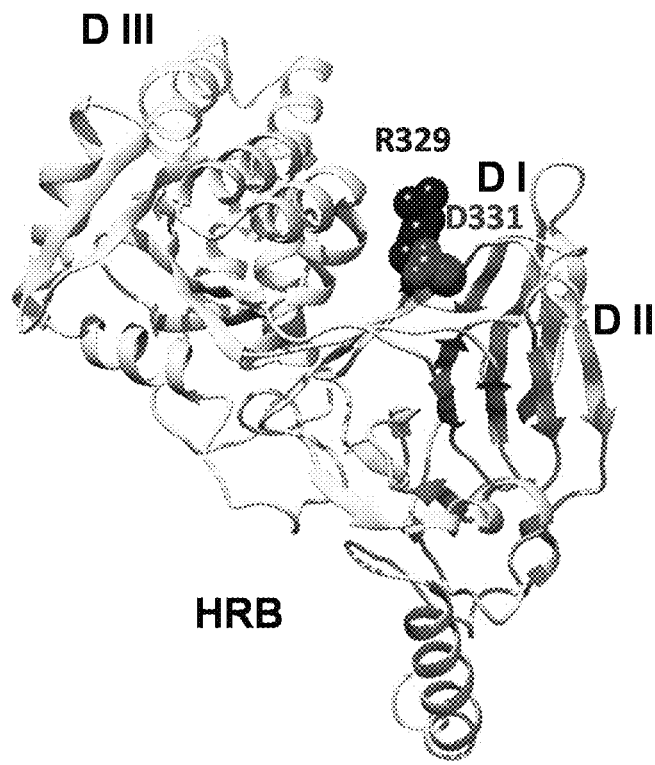
FIGS. 14A-14D: Location of RGD motif in the predicted structure of hMPV F protein.
Figure 14B:
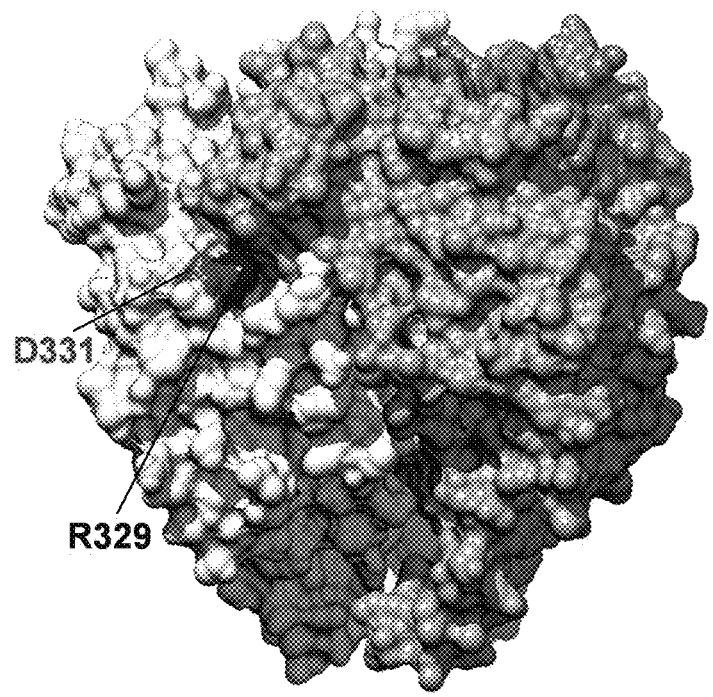
Figure 14C:
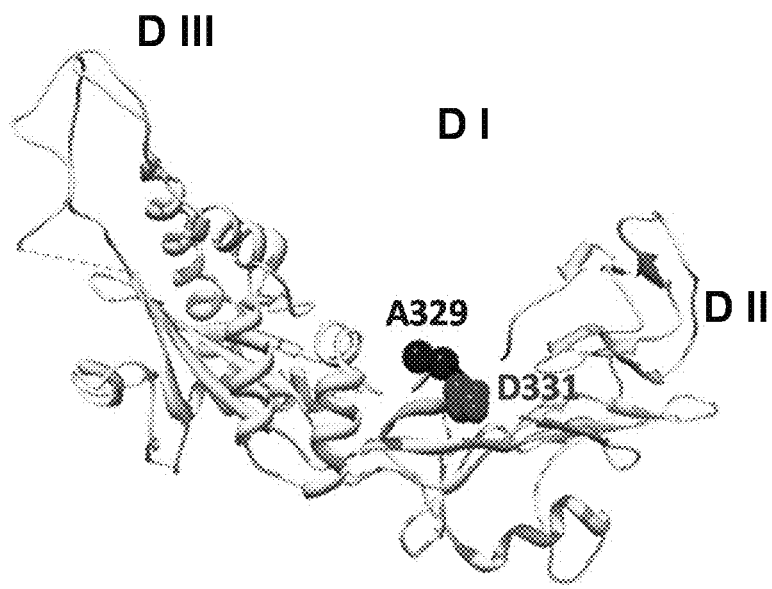
Figure 14D:
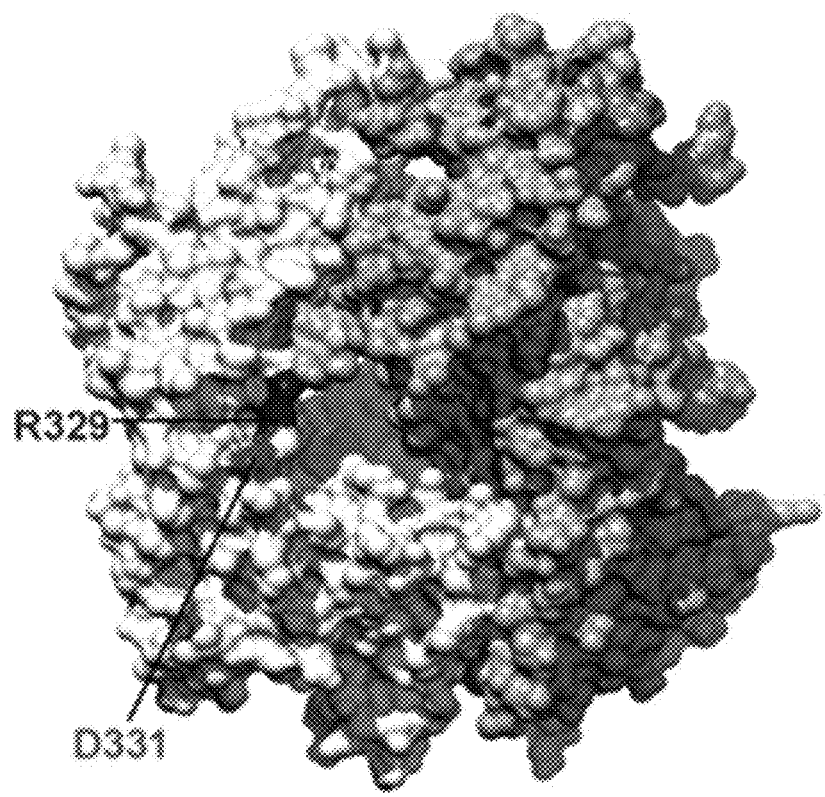

Since rhMPV-R329K and D331A were attenuated in cotton rats, the immunogenicity of these recombinant viruses was examined. Cotton rats were inoculated intranasally with wild-type rhMPV or rhMPV mutants. Serum samples were collected weekly for the detection of humoral immune response. At week 4 post-inoculation, animals were challenged with $10^6$ PFU of rhMPV. At day 4 post-challenge, all the animals were sacrificed and nasal turbinate and lung samples were collected for virus detection and pathological examination. As shown in FIG. 13, rhMPV-R329K and D331A elicited high levels of neutralizing antibody that were comparable to rhMPV. No hMPV-specific antibody was detected in unvaccinated control animals. As shown in Table 3, cotton rats vaccinated with rhMPV-D331A did not have any detectable infectious virus particles in either nasal turbinate or lungs after challenge with rhMPV on day 5. Only one out of five animals in the rhMPV-R329K vaccinated group had detectable virus in nasal turbinate but not in the lung. In contrast, unvaccinated challenge control had average titers of $10^{4.99}$ and $10^{4.74}$ in nasal turbinate and lung, respectively. Pulmonary histology showed that the unvaccinated challenged control had moderate pathological changes characterized by interstitial pneumonia, mononuclear cell infiltrate, and edematous thickening of the bronchial submucosa. In contrast, no or mild histological changes were found in the lungs of cotton rats vaccinated with rhMPV-R329K and D331A. Collectively, these results showed that rhMPV-R329K and D331A provided complete protection from virulent challenge and are potential vaccine candidates for hMPV.

TABLE 2

Pathogenesis of rhMPV mutants in cotton rats

| Mutant [A] | Number of cotton rats per group | Viral replication in nasal turbinate [B] | | Viral replication in lung [C] | | Lung histology [D] | Lung IHC [E] |
|---|---|---|---|---|---|---|---|
| | | % of infected animals | Mean titer log (PFU/g) | % of infected animals | Mean titer log (PFU/g) | | |
| rhMPV | 5 | 100 | 5.19 ± 0.48[a] | 100 | 4.08 ± 0.26[a] | 1.5[a] | 2.5[a] |
| R329K | 5 | 40 | 2.87[b] | 20 | 4.16[b] | 0.5[b] | 0.5[b] |
| D331A | 5 | 100 | 4.74 ± 0.43[a] | 40 | 2.1[b] | 0.6[b] | 0.5[b] |
| D331E | 5 | 100 | 5.12 ± 0.22[a] | 100 | 4.33 ± 0.51[a] | 1.2[a] | 2.5[a] |
| D331R | 5 | 100 | 5.20 ± 0.24[a] | 100 | 4.64 ± 0.27[a] | 1.0[a] | 3.0[a] |

[A] Cotton rats were inoculated intranasally with DMEM or $2 \times 10^5$ pfu wild-type rhMPV or rhMPV mutants. At day 4 post immunization, animals were euthanized for pathology study.
[B] For rhMPV-R329A, 2 out of 5 cotton rats had detectable virus with an average titer of 2.87 log. Value within a column followed by the different lowercase letters ([a] and [b]) are significantly different (P < 0.05).
[C] For rhMPV-R329K, 1 out of 5 cotton rats had detectable virus with a titer of 4.16 log. For rhMPV-D331A, 2 out of 5 cotton rats had detectable virus with an average titer of 2.1 log.
[D] The severity of lung histology was scored for each lung tissues. Average score for each group was shown. 0 = no change; 1 = mild change; 2 = moderate change; and 3 = severe change.
[E] The amount of hMPV antigen expression in lung was scored. Average score for each group was shown. 0 = no antigen; 1 = small amount; 2 = moderate amount; and 3 = large amount.

TABLE 3

Immunogenicity of mutant hMPVs in cotton rats

| Mutant [A] | Number of cotton rats per group | Nasal turbinate [B] | | Lung | | Lung histology [C] |
| --- | --- | --- | --- | --- | --- | --- |
| | | % of infected animals | Mean titer log (PFU/g) | % of infected animals | Mean titer log (PFU/g) | |
| DMEM | 5 | 100 | 4.99 ± 0.30 | 100 | 4.74 ± 0.50 | 1.5[a] |
| rhMPV | 5 | 0 | ND | 0 | ND | 0.5[b] |
| R329K | 5 | 20 | 4.27 | 0 | ND | 0.4[b] |
| D331A | 5 | 0 | ND | 0 | ND | 0.5[b] |

[A] Animals were immunized intranasally with DMEM or 2 × 10$^5$ pfu wild-type rhMPV or rhMPV mutants. At day 28 post immunization, animals were challenged with 10$^6$ pfu wild-type rhMPV.
[B] ND indicates non-detectable; 1 out of 5 cotton rats in rhMPV-R329K had detectable virus with a titer of 4.27 log.
[C] The severity of lung histology was scored for each lung tissues. Average score for each group was shown. 0 = no change; 1 = mild change; 2 = moderate change; and 3 = severe change. Value within a column followed by the different lowercase letters ([a] and [b]) are significantly different (P < 0.05).

Example 12

Discussion

This study demonstrated that α5β1 and αv integrins are essential for cell-cell fusion triggered by hMPV F protein. Moreover, it was shown that amino acid residues R329 and G330 within the putative integrin-binding motif ($^{329}$RGD$^{331}$) in the F protein play crucial roles in cell-cell fusion and viral infectivity. This conclusion is supported by multiple lines of evidence. First, hMPV F-mediated cell-cell fusion was inhibited by antibodies against integrin α5β1 or αv, as well as by siRNA-mediated knockdown of α5 or αv expression. Second, integrin α5β1 or αv-specific antibodies reduced hMPV infection and expression of integrin α5β1 on the cell surface enhanced hMPV infectivity in cell culture. Third, amino acid substitutions in R329 and G330 within the RGD motif of the F protein significantly impaired fusion activity. Fourth, mutations to the RGD motif that reduced fusion were either lethal to the virus or resulted in recombinant viruses (rhMPV-R329K and D331A) that were attenuated in viral replication in cell culture. Finally, recombinant rhMPV-R329K and D331A were attenuated in viral replication in a cotton rat model in vivo. Collectively, the data show that α5β1 and αv integrins serve as receptors for hMPV.

Integrins are a family of cell surface heterodimeric glycoproteins composed of 18 α and 8 β subunits that are expressed in nearly all cell types and facilitate cellular adhesion to and migration on the extracellular matrix proteins found in intercellular spaces and basement membranes. It was hypothesized that disruption of the interaction between integrin receptors and the RGD motif of hMPV F would inhibit fusion activity, which in turn would inhibit viral entry if integrin receptors play direct roles in viral attachment and entry. Since paramyxoviruses enter cells by fusing their viral envelope with a host cell membrane, the role of intergrin receptors and their RGD motif-binding activity can be directly measured by a cell-cell fusion assay. Using this assay, it was demonstrated that both αvβ1 and α5β1 integrin receptors are essential for cell-cell fusion mediated by hMPV F. Consistent with this, mutation of the integrin binding motif ($^{329}$RGD$^{331}$), especially residues R329 and G330, significantly inhibited cell-cell fusion without significantly altering cell surface expression of F protein. Replacing the positively charged side chain of R329 with an uncharged side chain (R329A) or a negatively charged side chain (R329D) abolished the ability of hMPV F protein to promote cell-cell fusion. No viable recombinant virus was recovered with these mutations, demonstrating that they are lethal to the virus. Similarly, introducing mutations at residue 330 (G330A or G330S) significantly impaired the fusion activity of hMPV F.

While recombinants rhMPV-G330A and G330S were successfully recovered, rhMPV-G330A replicated extremely poorly in cell culture and rhMPV-G330S is genetically unstable. Compared to R329 and G330, residue D331 plays a minor role in fusion. Substituting the negatively charged side chain of D331 with positively or negatively charged side chains (D331R and D331E) led to enhanced cell-cell fusion. Consistent with this, recombinant hMPVs carrying these mutations replicated as efficiently as wild-type hMPV in cell culture and in cotton rats. Previously, it was shown that D331A mutation retains approximately 80% of fusion activity, which was consistent with the present data. In addition, recombinant rhMPV-D331A were defective in viral replication in cell culture and cotton rats. Overall, the extent of fusion activity for each F mutant was consistent with its ability of replication in vitro and in vivo. For example, F mutants that promoted less than 20% of wt fusion activity were lethal to virus whereas F mutants (R329K and D331) had 60-70% of wild type fusion activity were attenuated in viral replication in cell culture and cotton rats. The present data show that residues R329 and G330 within the RGD motif are essential for cell-cell fusion and viability of the virus, and that the RGD motif in the F protein is required for hMPV infectivity in vitro and in vivo.

Although the RGD motif is conserved in a number of viral proteins, the contributions of these three residues to virus entry and infectivity differ from virus to virus. Many bacterial pathogens target cell adhesion molecules via integrin receptors to establish an intimate contact with host cells and tissues. Mutagenesis and biochemical studies have found that integrin receptors exhibited variable degree of affinity to the analogs or mutants of the RGD motif, depending on the property of integrin binding protein. Individual residues within RGD motif in surface proteins of many bacteria (such as Shigella, Leptospira, and Streptococcus species) played a dominant role in binding to integrin receptors. However, in the type IV secretion system (T4SS) protein CagL of Helicobacter pylori, all three residues in RGD motif are important for integrin binding as evidenced that alanine mutations to each of these residues abolished the adhesion function.

To gain possible structural insight into the role of the RGD motif in viral binding, a model structure of hMPV F protein was constructed using the atomic coordinates of the crystal structure of the prefusion form of RSV F protein as template (PDB ID: 4JHW) (FIG. 14). As in RSV F protein, each F monomer is composed of five well-structured domains, namely, DI-III, HRA and HRB, and one relatively loose loop connecting the C-terminus of DII and HRB, which has been named the 'HRB linker.' The RGD motif is located in the loop between strand β14 and β15 in the HRA region in the predicted structure of the hMPV F monomer (FIG. 14A). In the model structure of hMPV F trimer (FIGS. 14A-14B), the RGD motif is located in the contact region of each subunit of the F trimer. In addition, residues R329 and G330 are exposed on the surface of the F trimer, suggesting that the RGD motif may make contact with integrin receptors on the cell surface. An electrostatic interaction between R329 of the F protein and specific integrin subtypes and the small steric hindrance at D331 may favor integrin binding and the subsequent promotion of cell-cell fusion, whereas D331 may be not directly involved in binding to integrin.

The two most common vaccine strategies against infectious diseases are inactivated and live attenuated viruses. For safety, inactivated vaccines are generally preferred. However, development of an inactivated vaccine for human paramyxoviruses has been a problem. A formalin-inactivated RSV vaccine developed and tested in the 1960s not only failed to induce a protective immune response in a human trial, but led to enhanced respiratory disease upon natural infection with RSV. Another study showed that cotton rats immunized with formalin-inactivated hMPV vaccine were protected against infection, but developed increased lung damage. These observations suggest that, similar to RSV, an inactivated vaccine may not be the best choice for hMPV.

Like RSV, a live attenuated vaccine for hMPV would appear to be the best vaccine approach because enhanced lung damage has not been observed with virus infection of naïve animals, following challenge with the same virus. However, it has been technically difficult to isolate a virus that has an optimal balance between attenuation and immunogenicity. In the present study, recombinants rhMPV-R329K and D331A were significantly defective in viral replication in cell culture as well as in cotton rats. Cotton rats immunized with rhMPV-R329K and D331A not only triggered a high level of neutralizing antibody, but also provided complete protection against hMPV infection. These results showed that rhMPV-R329K and D331A are attenuated and retain high immunogenicity. Therefore, inhibition of the integrin-F protein interactions serves as an approach to attenuate hMPV for live attenuated vaccines.

Part II. Non-limiting examples of applications

Example 13

Therapeutics

Further described herein are methods for inducing a protective immune response against hMPV by administration to a mammal an effective amount of a pharmaceutical composition comprising a therapeutic compound, i.e., an immunogen. In one embodiment, the therapeutic is substantially purified. The mammal may be, but is not limited to, a cotton rat, or a primate, including rhesus or other macaque, African green monkey, chimpanzee, baboon, squirrel monkey, marmoset, mountain gorilla, and most preferably human.

Various delivery systems are useful to administer a pharmaceutical composition, e.g., emulsions, microspheres, immune-stimulating complexes, liposomes, virosomes, polymeric nanoparticles, micelles, dendrimers, etc. Methods of administration include, but are not limited to, intradermal, intramuscular, intraperitoneal, intravenous, subcutaneous, intranasal, and oral routes.

The pharmaceutical compositions are administered by any convenient route, for example by infusion or bolus injection, by absorption through epithelial or mucocutaneous linings (e.g., oral mucosa, rectal and intestinal mucosa, etc.) and may be administered together with other biologically active agents.

In a specific embodiment where the therapeutic compound is a nucleic acid encoding a protein therapeutic, the nucleic acid is administered in vivo by constructing it as part of an appropriate nucleic acid expression vector and administering it so that it becomes intracellular, or coating with lipids or cell-surface receptors or transfecting agents, or by administering it in linkage to a homeobox-like peptide which is known to enter the nucleus. Alternatively, a nucleic acid therapeutic can be introduced intracellularly and incorporated within host cell DNA for expression, by homologous recombination.

Example 14

Pharmaceutical Compositions

Pharmaceutical compositions comprise a therapeutically effective amount of a therapeutic compound, and a pharmaceutically acceptable carrier, vehicle, and/or excipient. Such a carrier includes, but is not limited to, saline, buffered saline, dextrose, water, glycerol, ethanol, and combinations thereof. The carrier and composition can be sterile. The formulation will suit the mode of administration.

In certain embodiments, the composition further comprises one or more adjuvants.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In one embodiment, the composition is formulated in accordance with routine procedures as a pharmaceutical composition adapted for intravenous administration to human beings. For example, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

Example 15

Kits

A composition, recombinant hMPV, or vaccine described herein may be provided in the form of a kit. In some embodiments, the kit provides the composition, recombinant hMPV, or vaccine and a pharmaceutically acceptable carrier, vehicle/and or excipient for administration to a mammal, most preferably a human Kits may further include a pharmaceutically acceptable adjuvant.

Components of a kit may be separately packaged or contained. The components of a kit may be mixed together prior to administration, or co-administered separately. Multiple separately packaged or contained doses of the composition, recombinant hMPV, or vaccine may be supplied in a kit if administration of one or more subsequent doses of the composition, recombinant hMPV, or vaccine is required.

The kits may include appropriate instructions for preparing the composition, recombinant hMPV, or vaccine for administration, and appropriate delivery means. The instructions may be in any suitable format, including, but not limited to, printed matter, videotape, computer readable disk, or optical disc.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

A deposit of the viruses of this invention is maintained by The Ohio State University, Columbus, Ohio. Access to this deposit will be available during the pendency of this application to persons determined by the Commissioner of Patents and Trademarks to be entitled thereto under 37 CFR § 1.14 and 35 USC § 122. Upon allowance of any claims in this application, all restrictions on the availability to the public of the variety will be irrevocably removed by affording access to a deposit of the viruses under the Budapest Treaty with the American Type Culture Collection, Manassas, Va.

The invention claimed is:

1. A composition comprising a live, attenuated human *metapneumovirus* (hMPV) comprising a mutated integrin-binding motif (RGD motif) in a fusion (F) protein of the live, attenuated hMPV, wherein the mutated RGD motif consists of a mutation or combination of mutations selected from: R329K; D331A; R329K and G330A; R329K and D331A; R329K and D331E; R329K and D331R; G330A and D331A; R329K, G330A, and D331A; R329K, G330A, and D331E; and R329K, G330A, and D331R.

2. The composition of claim 1, wherein the mutated RGD motif consists of an R329K mutation, a D331A mutation, or both an R329K mutation and a D331A mutation.

3. The composition of claim 1, wherein the mutated RGD motif consists of an R329K mutation.

4. The composition of claim 1, wherein the mutated RGD motif consists of a D331A mutation.

5. The composition of claim 1, wherein the composition is a pharmaceutical composition.

6. The composition of claim 1, wherein the composition is a vaccine.

7. A method for inducing a protective immune response against human *metapneumovirus* (hMPV) or for treating hMPV infection in a mammal comprising administering to the mammal a pharmaceutically effective dose of the composition of claim 1.

8. The method of claim 7, wherein the composition is administered orally, subcutaneously, or intranasally.

9. The method of claim 7, wherein the mammal is a human.

10. The method of claim 7, further comprising administering at least one subsequent pharmaceutically effective dose of the composition to the mammal.

11. The method of claim 10, wherein the at least one subsequent pharmaceutically effective dose is administered at a time interval selected from: approximately one week after the first dose; approximately two weeks after the first dose; approximately three weeks after the first dose; approximately four weeks after the first dose; approximately five weeks after the first dose; approximately six weeks after the first dose; approximately seven weeks after the first dose; and approximately eight weeks after the first dose.

12. A recombinant human *metapneumovirus* (hMPV) comprising a mutated integrin-binding motif (RGD motif) in a fusion (F) protein of the hMPV capable of inducing neutralizing antibody and a T cell immune response in a mammal without inducing clinical symptoms of hMPV infection, wherein the mutated RGD motif consists of a mutation or combination of mutations selected from R329K; D331A; R329K and G330A; R329K and D331A; R329K and D331E; R329K and D331R; G330A and D331A; R329K, G330A, and D331A; R329K, G330A, and D331E; and R329K, G330A, and D331R.

13. The recombinant hMPV of claim 12, wherein the recombinant hMPV is selected from rhMPV-R329K; and rhMPV-D331A.

14. The recombinant hMPV of claim 12, wherein the recombinant hMPV is rhMPV-R329K (SEQ ID NO: 2).

15. The recombinant hMPV of claim 12, wherein the recombinant hMPV is rhMPV-D331A (SEQ ID NO: 4).

16. The composition of claim 6, further comprising an adjuvant.

17. A method of preparing a pharmaceutical composition for inducing a protective immune response against human *metapneumovirus* (hMPV) in an individual in need thereof comprising mixing a composition of claim 1 with a suitable carrier, vehicle, and/or excipient.

18. The method according to claim 17, wherein the pharmaceutical composition is formulated for oral, subcutaneous, or intranasal administration.

19. A method of attenuating a human *metapneumovirus* (hMPV) comprising mutating an integrin-binding motif (RGD motif) in a fusion (F) protein of the hMPV, wherein the RGD motif comprises an R329K mutation, or an R329K mutation and a D331A mutation.

* * * * *

SEQUENCE LISTING

<160> NUMBER OF SEQ ID NOS: 13

<210> SEQ ID NO 1
<211> LENGTH: 1620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atgtcttgga aagtggtgat catttttttca ttgttaataa cacctcaaca cggtcttaaa      60
gagagctact tagaagagtc atgtagcact ataactgaag gatatctcag tgttctgagg     120
acaggttggt acaccaatgt ttttacactg gaggtaggcg atgtagagaa ccttacatgt     180
gccgatggac ccagcttaat aaaaacagaa ttagacctga ccaaaagtgc actaagagag     240
ctcagaacag tttctgctga tcaactggca agagaggagc aaattgaaaa tcccagacaa     300
tctagattcg ttctaggagc aatagcactc ggtgttgcaa ctgcagctgc agttacagca     360
ggtgttgcaa ttgccaaaac catccggctt gaaagtgaag taacagcaat taagaatgcc     420
ctcaaaaaga ccaatgaagc agtatctaca ttggggaatg gagttcgtgt gttggcaact     480
gcagtgagag agctgaaaga ttttgtgagc aagaatctaa cacgtgcaat caacaaaaac     540
aagtgcgaca ttgctgacct gaaaatggcc gttagcttca gtcaattcaa cagaaggttc     600
ctaaatgttg tgcggcaatt ttcagacaac gctggaataa caccagcaat atctttggac     660
ttaatgacag atgctgaact agccagagct gtttccaaca tgccaacatc tgcaggacaa     720
ataaaactga tgttggagaa ccgtgcaatg gtaagaagaa aagggttcgg attcctgata     780
ggagtttacg gaagctccgt aatttacatg gtgcaactgc caatctttgg ggttatagac     840
acgccttgct ggatagtaaa agcagcccct tcttgttcag gaaaaaaggg aaactatgct     900
tgcctcttaa gagaagacca aggatggtat tgtcaaaatg cagggtcaac tgtttactac     960
ccaaatgaaa aagactgtga aacaaaagga gaccatgtct tttgcgacac agcagcagga    1020
atcaatgttg ctgagcagtc aaaggagtgc aacataaaca tatctactac taattaccca    1080
tgcaaagtta gcacaggaag acatcctatc agtatggttg cactatctcc tcttgggcct    1140
ttggttgctt gctacaaggg agtgagctgt tccattggca gcaacagagt agggatcatc    1200
```

```
aagcaactga acaaaggctg ctcttatata accaaccaag acgcagacac agtgacaata    1260
gacaacactg tataccagct aagcaaagtt gaaggcgaac agcatgttat aaaaggaagg    1320
ccagtgtcaa gcagctttga cccagtcaag tttcctgaag atcaattcaa tgttgcactt    1380
gaccaagttt tcgagagcat tgagaacagt caggccttgg tggatcaatc aaacagaatc    1440
ctaagcagtg cagagaaagg aaacactggc ttcatcattg taataattct aattgctgtc    1500
cttggctcta ccatgatcct agtgagtgtt tttatcataa taaagaaaac aaagaaaccc    1560
acaggagcac ctccagagct gagtggtgtc acaaacaatg gcttcatacc acataattag    1620
```

<210> SEQ ID NO 2
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285
```

Ala Pro Ser Cys Ser Gly Lys Lys Gly Asn Tyr Ala Cys Leu Leu Arg
            290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Lys Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535

<210> SEQ ID NO 3
<211> LENGTH: 1620
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgtcttgga aagtggtgat cattttttca ttgttaataa cacctcaaca cggtcttaaa     60
gagagctact tagaagagtc atgtagcact ataactgaag gatatctcag tgttctgagg    120
acaggttggt acaccaatgt ttttacactg gaggtaggcg atgtagagaa ccttacatgt    180
gccgatggac ccagcttaat aaaaacagaa ttagacctga ccaaaagtgc actaagagag    240
ctcagaacag tttctgctga tcaactggca agagaggagc aaattgaaaa tcccagacaa    300
tctagattcg ttctaggagc aatagcactc ggtgttgcaa ctgcagctgc agttacagca    360
ggtgttgcaa ttgccaaaac catccggctt gaaagtgaag taacagcaat taagaatgcc    420
ctcaaaaaga ccaatgaagc agtatctaca ttggggaatg gagttcgtgt gttggcaact    480
gcagtgagag agctgaaaga ttttgtgagc aagaatctaa cacgtgcaat caacaaaaac    540
aagtgcgaca ttgctgacct gaaaatggcc gttagcttca gtcaattcaa cagaaggttc    600

```
ctaaatgttg tgcggcaatt ttcagacaac gctggaataa caccagcaat atctttggac    660
ttaatgacag atgctgaact agccagagct gtttccaaca tgccaacatc tgcaggacaa    720
ataaaactga tgttggagaa ccgtgcaatg gtaagaagaa aagggttcgg attcctgata    780
ggagtttacg gaagctccgt aatttacatg gtgcaactgc caatctttgg ggttatagac    840
acgccttgct ggatagtaaa agcagcccct tcttgttcag gaaaaaaggg aaactatgct    900
tgcctcttaa gagaagacca aggatggtat tgtcaaaatg cagggtcaac tgtttactac    960
ccaaatgaaa aagactgtga acaagagga gcccatgtct tttgcgacac agcagcagga   1020
atcaatgttg ctgagcagtc aaaggagtgc aacataaaca tatctactac taattaccca   1080
tgcaaagtta gcacaggaag acatcctatc agtatggttg cactatctcc tcttggggct   1140
ttggttgctt gctacaaggg agtgagctgt tccattggca gcaacagagt agggatcatc   1200
aagcaactga acaaggctg ctcttatata accaaccaag acgcagacac agtgacaata   1260
gacaacactg tataccagct aagcaaagtt gaaggcgaac agcatgttat aaaaggaagg   1320
ccagtgtcaa gcagctttga cccagtcaag tttcctgaag atcaattcaa tgttgcactt   1380
gaccaagttt tcgagagcat tgagaacagt caggccttgg tggatcaatc aaacagaatc   1440
ctaagcagtg cagagaaagg aaacactggc ttcatcattg taataattct aattgctgtc   1500
cttggctcta ccatgatcct agtgagtgtt tttatcataa taaagaaaac aaagaaaccc   1560
acaggagcac ctccagagct gagtggtgtc acaaacaatg gcttcatacc acataattag   1620

<210> SEQ ID NO 4
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Trp Lys Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
                20                  25                  30

Glu Gly Tyr Leu Ser Val Leu Arg Thr Gly Trp Tyr Thr Asn Val Phe
            35                  40                  45

Thr Leu Glu Val Gly Asp Val Glu Asn Leu Thr Cys Ala Asp Gly Pro
        50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175
```

```
Ile Asn Lys Asn Lys Cys Asp Ile Ala Asp Leu Lys Met Ala Val Ser
            180                 185                 190
Phe Ser Gln Phe Asn Arg Arg Phe Leu Asn Val Val Arg Gln Phe Ser
        195                 200                 205
Asp Asn Ala Gly Ile Thr Pro Ala Ile Ser Leu Asp Leu Met Thr Asp
    210                 215                 220
Ala Glu Leu Ala Arg Ala Val Ser Asn Met Pro Thr Ser Ala Gly Gln
225                 230                 235                 240
Ile Lys Leu Met Leu Glu Asn Arg Ala Met Val Arg Arg Lys Gly Phe
                245                 250                 255
Gly Phe Leu Ile Gly Val Tyr Gly Ser Ser Val Ile Tyr Met Val Gln
            260                 265                 270
Leu Pro Ile Phe Gly Val Ile Asp Thr Pro Cys Trp Ile Val Lys Ala
        275                 280                 285
Ala Pro Ser Cys Ser Gly Lys Lys Gly Asn Tyr Ala Cys Leu Leu Arg
    290                 295                 300
Glu Asp Gln Gly Trp Tyr Cys Gln Asn Ala Gly Ser Thr Val Tyr Tyr
305                 310                 315                 320
Pro Asn Glu Lys Asp Cys Glu Thr Arg Gly Ala His Val Phe Cys Asp
                325                 330                 335
Thr Ala Ala Gly Ile Asn Val Ala Glu Gln Ser Lys Glu Cys Asn Ile
            340                 345                 350
Asn Ile Ser Thr Thr Asn Tyr Pro Cys Lys Val Ser Thr Gly Arg His
        355                 360                 365
Pro Ile Ser Met Val Ala Leu Ser Pro Leu Gly Ala Leu Val Ala Cys
    370                 375                 380
Tyr Lys Gly Val Ser Cys Ser Ile Gly Ser Asn Arg Val Gly Ile Ile
385                 390                 395                 400
Lys Gln Leu Asn Lys Gly Cys Ser Tyr Ile Thr Asn Gln Asp Ala Asp
                405                 410                 415
Thr Val Thr Ile Asp Asn Thr Val Tyr Gln Leu Ser Lys Val Glu Gly
            420                 425                 430
Glu Gln His Val Ile Lys Gly Arg Pro Val Ser Ser Ser Phe Asp Pro
        435                 440                 445
Val Lys Phe Pro Glu Asp Gln Phe Asn Val Ala Leu Asp Gln Val Phe
    450                 455                 460
Glu Ser Ile Glu Asn Ser Gln Ala Leu Val Asp Gln Ser Asn Arg Ile
465                 470                 475                 480
Leu Ser Ser Ala Glu Lys Gly Asn Thr Gly Phe Ile Ile Val Ile Ile
                485                 490                 495
Leu Ile Ala Val Leu Gly Ser Thr Met Ile Leu Val Ser Val Phe Ile
            500                 505                 510
Ile Ile Lys Lys Thr Lys Lys Pro Thr Gly Ala Pro Pro Glu Leu Ser
        515                 520                 525
Gly Val Thr Asn Asn Gly Phe Ile Pro His Asn
    530                 535
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 5

His His His His His His
1               5

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggaattcgc caccatgtct tggaaagtgg tgatc                              35

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ataagaatgc ggccgcttag tgatggtgat ggtgatggcc agtgtttcct ttctctgc     58

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggaattcat gtcttggaaa gtggtgatc                                     29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgctcgagc taattatgtg gtatgaagc                                     29

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttataataca cgtctgcgcc c                                             21

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
caccgccggg aaaatca                                                       17

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccttcagtt gggaaatttg g                                                  21

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
atttgcagca gtccc                                                         15
```

UNITED STATES PATENT AND TRADEMARK OFFICE
CERTIFICATE OF CORRECTION

| | |
|---|---|
| PATENT NO. | : 10,093,702 B2 |
| APPLICATION NO. | : 14/777095 |
| DATED | : October 9, 2018 |
| INVENTOR(S) | : Jianrong Li et al. |

It is certified that error appears in the above-identified patent and that said Letters Patent is hereby corrected as shown below:

In the Specification

At Column 1, Line 12, please insert the following paragraph:
--GOVERNMENT LICENSE RIGHTS
This invention was made with government support under AI090060 awarded by the National Institutes of Health. The government has certain rights in the invention.--

Signed and Sealed this
Eighteenth Day of July, 2023

*Katherine Kelly Vidal*

Katherine Kelly Vidal
*Director of the United States Patent and Trademark Office*